(12) United States Patent
Lee et al.

(10) Patent No.: US 9,057,725 B2
(45) Date of Patent: Jun. 16, 2015

(54) COMPOSITION FOR DIAGNOSING, TREATING, AND PREVENTING LIVER DISEASE

(75) Inventors: Jung Weon Lee, Seoul (KR); Ki Hun Park, Gyeongsangnam-do (KR); Min Kyung Kang, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/813,135

(22) PCT Filed: Jul. 22, 2011

(86) PCT No.: PCT/KR2011/005444
§ 371 (c)(1),
(2), (4) Date: Mar. 21, 2013

(87) PCT Pub. No.: WO2012/015200
PCT Pub. Date: Feb. 2, 2012

(65) Prior Publication Data
US 2013/0178533 A1 Jul. 11, 2013

(30) Foreign Application Priority Data

Jul. 30, 2010 (KR) .................. 10-2010-0074256
Dec. 9, 2010 (KR) .................. 10-2010-0125743
Jul. 22, 2011 (KR) .................. 10-2011-0072902

(51) Int. Cl.
| | |
|---|---|
| *G01N 33/563* | (2006.01) |
| *A61K 39/395* | (2006.01) |
| *A61K 39/00* | (2006.01) |
| *G01N 33/68* | (2006.01) |
| *G01N 33/50* | (2006.01) |
| *A61K 31/18* | (2006.01) |

(52) U.S. Cl.
CPC .......... *G01N 33/563* (2013.01); *G01N 33/6893* (2013.01); *G01N 33/5067* (2013.01); *G01N 2800/085* (2013.01); *A61K 31/18* (2013.01)

(58) Field of Classification Search
None
See application file for complete search history.

(56) References Cited

U.S. PATENT DOCUMENTS

2011/0086342 A1 * 4/2011 Esumi et al. ............... 435/6

FOREIGN PATENT DOCUMENTS

| WO | WO 03/037315 A1 | 5/2003 |
| WO | WO 2008069608 A1 * | 6/2008 |

OTHER PUBLICATIONS

Lee et al. (2009), Hepatology, vol. 49, pp. 1316-1325.*
S. Cannito et al., "Epithelial-Mesenchymal Transition: From Molecular Mechanisms, Redox Regulation to Implications in Human Health and Disease," Antioxidants & Redox Signaling 12(12):1383-1432, 2010.
Müller-Pillasch et al. (1998), "Identification of a new tumour-associated antigen *TM4SF5* and its expression in human cancer," Gene 208: 25-30.
Lee et al. (2008), "Tetraspanin TM4SF5 mediates loss of contact inhibition through epithelial-mesenchymal transition in human hepatocarcinoma," The Journal of Clinical Investigation, 118(4):1354-1366.
International Search Report for PCT/KR2011/005444, mailed Jul. 27, 2012.

* cited by examiner

*Primary Examiner* — Christine J Saoud
*Assistant Examiner* — Jegatheesan Seharaseyon
(74) *Attorney, Agent, or Firm* — Lathrop & Gage LLP

(57) ABSTRACT

A composition for diagnosing, treating, and preventing liver disease, more particularly a composition for diagnosing liver disease comprising a material for measuring the grade of TM4SF5 (transmembrane 4 L six family member 5 or four-transmembrane L6 superfamily member 5) protein, a kit for diagnosing liver disease comprising the composition, a method for providing information necessary for diagnosing liver disease composed of the following steps: measuring the level of TM4SF5 protein and the expressions and phosphorylations of TM4SF5 expression related signaling proteins; and comparing the measured levels with those of the normal control, a method for screening a material for treating liver disease, and a composition for treating or preventing liver disease comprising a material inhibiting TM4SF5 protein expression or the expressions and phosphorylations of TM4SF5 expression related signaling proteins.

4 Claims, 29 Drawing Sheets

Figure 22
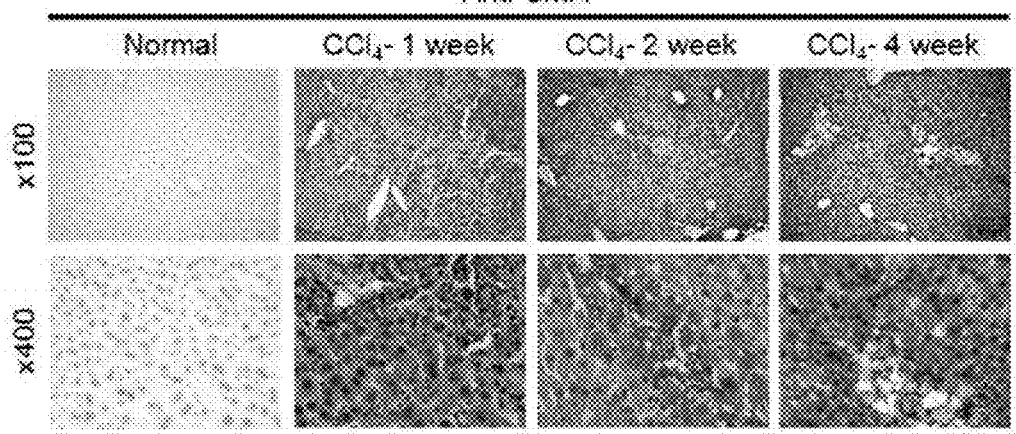
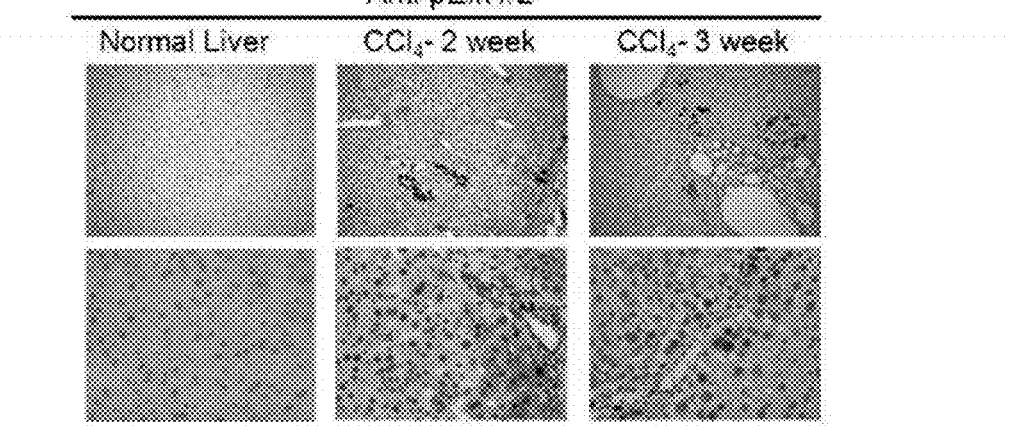

SEQUENCE LISTING

```
<160> NUMBER OF SEQ ID NOS: 2

<210> SEQ ID NO 1
<211> LENGTH: 708
<212> TYPE: DNA
<213> ORGANISM: Homo sapiens

<400> SEQUENCE: 1
actcaccgcc tgtccttcct gacacctcac catgtgtacg ggaaaatgtg cccgctgtgt      60
ggggctctcc ctcattaccc tctgcctcgt ctgcattgtg gccaacgccc tcctgctggt     120
acctaatggg gagacctcct ggaccaacac caaccatctc agcttgcaag tctggctcat     180
gggcggcttc attggcgggg gcctaatggt actgtgtccg gggattgcag ccgttcgggc     240 aggggcaag ggctgctgtg gtgctgggtg ctgtggaaac cgctgcagga tgctgcgctc      300
ggtcttctcc tcggcgttcg gggtgcttgg tgccatctac tgcctctcgg tgtctggagc     360
tgggctccga aatggaccca gatgcttaat gaacggcgag tggggctacc acttcgaaga     420
caccgcggga gcttacttgc tcaaccgcac tctatgggat cggtgcgagg cgcccctcg      480 cgtggtcccc tggaatgtga cgctcttctc gctgctggtg gccgcctcct gcctggagat     540
agtactgtgt gggatccagc tggtgaacgc gaccattggt gtcttctgcg gcgattgcag     600
gaaaaaacag gacacacctc actgaggctc cactgaccgc cgggttacac ctgctccttc     660
ctggacgctc actcccttgc tcgctagaat aaactgcttt gcgctctc                  708

<210> SEQ ID NO 2
<211> LENGTH: 197
<212> TYPE: PRT
<213> ORGANISM: Homo sapiens

<400> SEQUENCE: 2

Met Cys Thr Gly Lys Cys Ala Arg Cys Val Gly Leu Ser Leu Ile Thr
```

```
1               5                   10                  15
Leu Cys Leu Val Cys Ile Val Ala Asn Ala Leu Leu Val Pro Asn
            20                  25              30

Gly Glu Thr Ser Trp Thr Asn Thr Asn His Leu Ser Leu Gln Val Trp
        35              40              45

Leu Met Gly Gly Phe Ile Gly Gly Gly Leu Met Val Leu Cys Pro Gly
    50              55              60

Ile Ala Ala Val Arg Ala Gly Gly Lys Gly Cys Cys Gly Ala Gly Cys
65              70              75              80

Cys Gly Asn Arg Cys Arg Met Leu Arg Ser Val Phe Ser Ser Ala Phe
            85              90              95

Gly Val Leu Gly Ala Ile Tyr Cys Leu Ser Val Ser Gly Ala Gly Leu
            100             105             110

Arg Asn Gly Pro Arg Cys Leu Met Asn Gly Glu Trp Gly Tyr His Phe
            115             120             125

Glu Asp Thr Ala Gly Ala Tyr Leu Leu Asn Arg Thr Leu Trp Asp Arg
        130             135             140

Cys Glu Ala Pro Pro Arg Val Val Pro Trp Asn Val Thr Leu Phe Ser
145             150             155             160

Leu Leu Val Ala Ala Ser Cys Leu Glu Ile Val Leu Cys Gly Ile Gln
                165             170             175

Leu Val Asn Ala Thr Ile Gly Val Phe Cys Gly Asp Cys Arg Lys Lys
            180             185             190

Gln Asp Thr Pro His
        195
```

COMPOSITION FOR DIAGNOSING, TREATING, AND PREVENTING LIVER DISEASE

CROSS-REFERENCE TO RELATED APPLICATIONS

This application is a U.S. National Stage Application under 35 U.S.C. §371 of International Application No. PCT/KR2011/005444, filed Jul. 22, 2011, which claims the benefit of Korean Application No. 10-2010-0074256, filed Jul. 30, 2010; Korean Application No. 10-2010-0125743, filed Dec. 9, 2010; and Korean Application No. 10-2011-0072902, filed Jul. 22, 2011. All of these applications are hereby incorporated by reference in their entireties.

BACKGROUND OF THE INVENTION

1. Field of the Invention

The present invention relates to a composition for diagnosing, treating, and preventing liver disease, more precisely, a composition for diagnosing liver disease comprising a material for measuring TM4SF5 (Transmembrane 4 L six family member 5 or Four-Transmembrane L6 Superfamily member 5) protein grade, a kit for diagnosing liver disease containing the said composition, a method for providing information for diagnosing liver disease which is characterized by measuring the grade of TM4SF5 protein and the expressions of TM4SF5 expression related signaling proteins and the grade of phosphorylation to compare with those of the normal control group sample, a method for screening a material for treating liver disease, and a composition for treating or preventing liver disease containing a material inhibiting the expressions of TM4SF5 protein and TM4SF5 expression related signaling proteins and phosphorylation as well.

2. Description of the Related Art

The liver is a very important organ that is functioning in relation to many mechanisms in our body including lipid metabolism, detoxification, biliary excretion, storage of various nutritions, hematosis, blood clotting, regulation of circulating blood volume, etc. Therefore, once the liver is damaged, many functions become weak and if the damage or disorder gets worse, life itself will be in danger.

Functions of the liver are described hereinafter in more detail. First, the liver is functioning to control energy metabolism. That is, every nutrient absorbed from food is metabolized into energy producing materials in the liver, which are supplied to every part of the whole body or stored therein. Second, the liver is functioning to synthesize approximately 2,000 kinds of enzymes, serum proteins such as albumin and coagulation factors, bile acid, and lipids such as phospholipid and cholesterol, and store and distribute them as well. Third, the liver has detoxification and decomposition activities. Particularly, the liver is functioning to detoxify drugs, alcohol, and other toxic materials, because of which the liver is easily damaged, leading to drug-induced, toxic, and alcoholic liver diseases. In addition, the liver is involved in the excretion of metabolites to the duodenum and also involved in immune system, suggesting that the liver plays an important role in maintaining life system.

Liver disease is classified into viral liver disease, alcoholic liver disease, drug-induced toxic liver disease, fatty liver, autoimmune liver disease, metabolic liver disease, and other liver disease according to the cause. Liver disease does not show any subjective symptoms in the early stage. Only when the liver disease is already progressed, it is detected. Therefore, liver disease is the top reason of death not only domestically but also world-widely, requiring the development of an effective diagnosis and treatment method.

When the liver gets stimuli such as alcohol, virus, and other toxic environmental factors, hepatic stellate cells become activated to secret various cytokines including TGFβ. In particular, TGFβ (transforming growth factor β) is a multi-functional cytokine which has been known to play a critical role in development and carcinogenesis. In TGFβ signal transduction system, TGFβ receptor is activated by TGFβ, and the activated TGFβ receptor induces phosphorylation and activation of intracellular Smad2/3 protein. Then, the receptor is conjugated with Smad4, which is transferred into nucleus to cause transcriptions of related genes.

The secreted TGFβ accelerates collagen synthesis to induce hepatic fibrosis and to affect not only hepatic stellate cells but also surrounding hepatocytes to cause EMT (epithelial to mesenchymal transition). The continued hepatic fibrosis results in liver cirrhosis in the end. Thus, it is a very basic step to study and understand hepatic fibrosis process in order to understand any possible reason to cause liver cirrhosis.

Alcoholic hepatic injury is caused by those compounds generated by alcohol itself or alcohol metabolism, which causes lipidosis, hepatic injury, and hepatic fibrosis. When hepatocytes are injured by various reasons such as alcohol, chronic hepatitis B, chronic hepatitis C, chronic autoimmune disease, chronic biliary disease, chronic heart disease, parasite, and drug addiction, etc, various cytokines and oxygen free radicals are generated by the interactions of hepatocytes, Kupffer cells, sinusoidal endothelial cells, and hepatic stellate cells (HSC), leading to the damage of normal extracellular matrix (ECM). Furthermore, abnormal proliferation of ECM such as collagen I and collagen III progresses to hepatic fibrosis. Unlike liver cirrhosis, hepatic fibrosis is reversible and is composed of thin fibril without nodule formation. Once the cause of hepatic injury is eliminated, hepatic fibrosis becomes reversed to normal. However, hepatic fibrosis is continuously repeated, crosslinking between ECM increases to form thick fibril, resulting in irreversible liver cirrhosis with nodules. The increase of ECM such as collagen is an important reason of hepatic fibrosis which is produced by HSC activated by various reasons.

As hepatic fibrosis is more progressed, liver cirrhosis is developed. Once hepatic necrosis occurs by any reason, hepatic regeneration and fibrosis are developed. If those processes are repeated continuously, liver cirrhosis is developed. Liver cirrhosis, which is formed by hepatic nodules developed by continuous or repeated diffused hepatic injury, fibrosis and hepatic regeneration, is a chronic disease accompanied by necrosis, inflammation, and fibrosis, which eventually progresses to even fatal liver cancer.

TM4SF5 (Four-Transmembrane L6 Superfamily member 5) known as a kind of tetraspanins (or tetraspan) is a water insoluble protein, which is structured by four transmembrane regions, two extracellular rings, one intracytoplasmic ring, and two terminal regions. TM4SF5 proteins form conjugates with cell adhesion molecules such as integrin on cell membrane to form a huge tetraspanin-web or tetraspanin-enriched microdomain (TERM), contributing to various biological functions such as cell adhesion, cell proliferation, and cell migration, etc. It has been known that TM4SF5 is over-expressed in human liver cancer cells and is functioning as a carcinogen by inducing the accumulation of $p27^{kip1}$ protein in cytoplasm and accordingly inhibiting RhoA protein activity, leading to EMT and contact growth inhibition.

However, it has not been disclosed yet how TM4SF5 expression is induced by which signal transduction pathway, and how TM4SF5 is related to liver disease that progresses hepatic fibrosis and liver cirrhosis. Therefore, the present inventors investigated and confirmed that TGFβ induced TM4SF5 expression in the progress of liver disease and further completed this invention by confirming that TM4SF5 could be used as a marker for the diagnosis of liver disease and TM4SF5 antagonist could be used for the prevention and/or treatment of liver disease.

SUMMARY OF THE INVENTION

It is an object of the present invention to provide a composition for diagnosing liver disease comprising a material for measuring the grade of TM4SF5 (Transmembrane 4 L six family member 5 or Four-Transmembrane L6 Superfamily member 5) protein and/or the expression and phosphorylation of TM4SF5 expression related signaling protein, and a kit for diagnosing liver disease comprising the said composition for diagnosing liver disease above.

It is another object of the present invention to provide a method for providing information for diagnosing liver disease comprising the following steps:

1) measuring the grade of TM4SF5 protein in the biological sample separated from a subject with suspected liver disease; and 2) comparing the grade of TM4SF5 protein measured in step 1) with that of the normal control sample.

It is also an object of the present invention to provide a method for screening a material for treating liver disease comprising the following steps:

1) treating candidate materials for treating liver disease to hepatocytes expressing TM4SF5; and 2) selecting the candidate material that is confirmed to inhibit the expression of TM4SF5 protein, as the material for treating liver disease, by comparing that of the control group not treated with the candidate materials of step 1).

It is further an object of the present invention to provide a method for screening a material for treating liver disease comprising the following steps:

1) constructing an animal model induced with liver disease and hepatic injury by injecting or administering a drug such as $CCl_4$, followed by treating candidate materials for treating liver disease to the animal model; and 2) selecting the candidate material for treating liver disease that is confirmed to change the expression levels of one or more proteins selected from the group consisting of α-SMA, vimentin, cytoskeleton-intermediate filament, snail, slug, E-adherin, ZO-1, beta-catenin, desmoplakin, claudin, and collagen, which is caused by TM4SF5 expression, as the material for treating liver disease, by comparing with those of the control group not treated with the candidate materials of step 1).

It is also an object of the present invention to provide a composition for the treatment or prevention of liver disease comprising a material inhibiting TM4SF5 protein expression or activity.

It is also an object of the present invention to provide a material for measuring the grade of TM4SF5 protein, which can be used as a composition for diagnosing liver disease.

It is also an object of the present invention to provide a material inhibiting TM4SF5 expression or activity for the preparation of a drug for the treatment or prevention of liver disease.

It is also an object of the present invention to provide a method for treating liver disease containing the step of administering a pharmaceutically effective dose of a material inhibiting TM4SF5 expression or activity to a subject with liver disease.

It is also an object of the present invention to provide a method for preventing liver disease containing the step of administering a pharmaceutically effective dose of a material inhibiting TM4SF5 expression or activity to a subject.

To achieve the above objects, the present invention provides a composition for diagnosing liver disease comprising a material for measuring the grade of TM4SF5 (Transmembrane 4 L six family member 5 or Four-Transmembrane L6 Superfamily member 5) protein and/or the expression and phosphorylation of TM4SF5 expression related signaling protein.

The present invention also provides a kit for diagnosing liver disease comprising the said composition.

The present invention also provides a method for providing information for diagnosing liver disease comprising the following steps:

1) measuring the grade of TM4SF5 protein in the biological sample separated from a subject with suspected liver disease; and 2) comparing the grade of TM4SF5 protein measured in step 1) with that of the normal control sample.

The present invention also provides a method for screening a material for treating liver disease comprising the following steps:

1) treating candidate materials for treating liver disease to hepatocytes expressing TM4SF5; and 2) selecting the candidate material that is confirmed to inhibit the expression of TM4SF5 protein as the material for treating liver disease, by comparing that of the control group not treated with the candidate materials of step 1).

The present invention also provides a method for screening a material for treating liver disease comprising the following steps:

1) constructing an animal model induced with liver disease and hepatic injury by injecting or administering a drug such as $CCl_4$, followed by treating candidate materials for treating liver disease to the animal model; and 2) selecting the candidate material for treating liver disease that is confirmed to change the expression levels of one or more proteins selected from the group consisting of α-SMA, vimentin, cytoskeleton-intermediate filament, snail, slug, E-adherin, ZO-1, beta-catenin, desmoplakin, claudin, and collagen, which is caused by TM4SF5 expression, as the material for treating liver disease, by comparing with those of the control group not treated with the candidate materials of step 1).

The present invention also provides a composition for the treatment or prevention of liver disease comprising a material inhibiting TM4SF5 expression or activity.

The present invention also provides a material for measuring TM4SF5 protein level, which can be used as a composition for diagnosing liver disease.

The present invention also provides a material inhibiting TM4SF5 expression or activity for the preparation of a drug for the treatment or prevention of liver disease.

The present invention also provides a method for treating liver disease containing the step of administering a pharmaceutically effective dose of a material inhibiting TM4SF5 expression or activity to a subject with liver disease.

In addition, the present invention provides a method for preventing liver disease containing the step of administering a pharmaceutically effective dose of a material inhibiting TM4SF5 expression or activity to a subject.

Advantageous Effect

As explained hereinbefore, the screening of a material for the diagnosis and treatment of liver disease has been made possible by measuring the grade of TM4SF5 protein and/or the expression and phosphorylation levels of TM4SF5 expression related signaling proteins. It has also been made possible to prevent and/or treat liver disease by suppressing TM4SF5 expression or by using an antagonist against TM4SF5.

BRIEF DESCRIPTION OF THE DRAWINGS

The application of the preferred embodiments of the present invention is best understood with reference to the accompanying drawings, wherein:

FIG. 1 is a set of photographs illustrating the results of Western blotting showing Smad phosphorylation and TM4SF5 expression levels in human normal liver tissues and liver cancer tissues as well.

FIG. 2 is a graph illustrating the results of luciferase reporter gene assay performed to confirm the transcriptional activity of TM4SF5 promoter according to the treatment of TGFβ to Huh7, HepG2, and SNU16mAD cells.

FIG. 3 is a set of photographs illustrating the results of Western blotting performed to confirm the expression levels of vimentin, E-adherin and TM4SF5 and the phosphorylation levels of Smad3 and Smad2 in AML12 cells after the treatment of TGFβ and also the results of immunofluorescence assay using vimentin antibody confirming that the cell pattern changes into more dispersed pattern and vimentin expression increases over the treatment of TGFβ.

FIG. 4 is a set of photographs illustrating the results of Western blotting performed to confirm the increase of phosphorylation levels of Smad3 and Smad2 and the increase of TM4SF5 expression in Chang cells according to the treatment of TGFβ, and also showing the results of observation under optical microscope confirming the dispersed cell pattern.

FIG. 22 is a set of photographs illustrating the results of immunohistochemical staining performed to confirm the levels of α-SMA expression and Erk1/2 phosphorylation in liver tissues of normal mice and $CCl_4$ treated mice.

DESCRIPTION OF THE PREFERRED EMBODIMENTS

Figure 1:
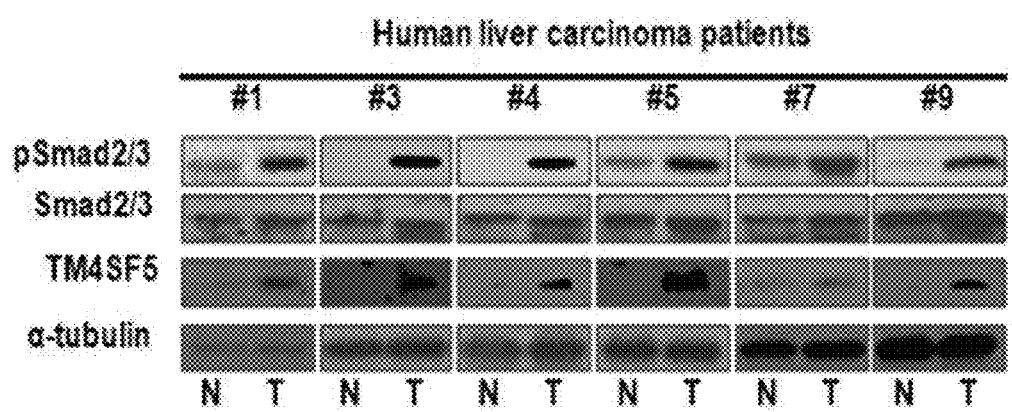
FIG. 1~FIG. 4 illustrate that TM4SF5 expression and EMT are induced by TGFβ.

The terms used in this invention are described hereinafter.

In this invention, the term "TM4SF5 protein" indicates a protein belongs to Transmembrane 4 L six family (Four Transmembrane L6 Superfamily member 5 or L6H), which is a member of the membrane receptor group able to pass through cell membrane 4 times, comprising tetraspanin, tetraspan or transmembrane 4 Super family (TM4SF). Such TM4SF (transmembrane 4 superfamily) proteins have similar structures that allow 4 times of transpassing cell membrane. That is, they share the structure having 4 hydrophobic regions which are suspected biochemically as transmembrane domains. Biochemical functions of Four-transmembrane L6 superfamily (including L6, TM4SF5, L6D, and IL-TMP) have not been disclosed yet.

In this invention, the term "prevention" or "preventing" indicates all the action taken to inhibit or delay the decrease of liver function by administering a composition.

In this invention, the term "treatment" or "treating" indicates all the action taken to recover or help liver function and liver growth by administering a material for treating.

In this invention, the term "administration" or "administering" indicates providing the composition of the present invention to a subject through a proper method.

Hereinafter, the present invention is described in detail.

The present invention provides a composition for diagnosing liver disease comprising a material for measuring the grade of TM4SF5 (Transmembrane 4 L six family member 5 or Four-Transmembrane L6 Superfamily member 5) protein.

The present invention also provides a material for measuring the grade of TM4SF5 protein, which can be used as a composition for diagnosing liver disease.

The said TM4SF5 protein is preferably obtained from the polypeptide having the amino acid sequence represented by SEQ. ID. NO: 2 expressed from the polynucleotide represented by SEQ. ID. NO: 1, but not always limited thereto.

The said TM4SF5 is a water-insoluble protein having 4 transmembrane domains, two extracellular rings, and two intracytoplasmic terminal domains in its structure, which has been known to be highly expressed in various cancer cells including pancreatic cancer cells, lung cancer cells, stomach cancer cells, rectal cancer cells, and liver cancer cell, etc (Muller-Pillasch, F., et al., Gene 208:25, 1998; Pascual-Le Tallec, L. et al., J Clin Endocrinol Metab 87:501, 2002).

The said "liver disease" herein indicates all the disease showing liver dysfunction, which is induced by virus (for example, A, B, C, D, or E type virus), alcohol, aplatoxin, drugs (antituberculosis drug, aspirin, antibiotics, anesthetics, antihypersentive, oral contraception, etc), and congenital metabolic abnormality, etc. Liver disease is exemplified by chronic hepatic injury, hepatic fibrosis, liver cirrhosis, hepatitis, liver cancer, alcoholic liver disease, and fatty liver, etc.

In this invention, the material for measuring the level of protein expression of each gene includes polyclonal antibody, monoclonal antibody, and recombinant antibody which are specifically recognizing TM4SF5 protein and conjugating thereto. The term "antibody" herein indicates a specific protein molecule presented against the antigenic region. As explained hereinbefore, since the marker protein for diagnosing liver disease has been identified, the antibody can be easily prepared using the marker protein according to the conventional method well-known to those in the art.

The said polyclonal antibody can be produced by the conventional method well-known to those in the art, which is precisely obtained from serum containing antibody taken from blood sample obtained from an animal injected with TM4SF5 antigen. Such polyclonal antibody can be produced by using random animal hosts including goat, rabbit, sheep, monkey, horse, pig, rat, cow, dog, etc.

The said monoclonal antibody can be produced by the conventional method such as hybridoma method [see Kohler and Milstein (1976) European Journal of Immunology 6:511-519] or phage antibody library technique (Clackson et al, Nature, 352:624-628, 1991; Marks et al, J. Mol. Biol., 222: 58, 1-597, 1991). The antibody produced by the above method can be separated and purified by gel electrophoresis, dialysis, salt precipitation, ion exchange chromatography, and affinity chromatography.

The antibody of the present invention includes not only complete antibody having 2 total length light chains and 2 total length heavy chains but also functional fragments of the antibody molecule. The functional fragment of the antibody molecule indicates the fragment at least has antigen binding function, which is exemplified by Fab, F(ab'), F(ab')2, and Fv, etc.

In a preferred embodiment of the present invention, it was confirmed that TGFβ induced TM4SF5 (Transmembrane 4 L six family member 5 or Four-Transmembrane L6 Superfamily member 5) expression in the developmental process of such liver disease as hepatic fibrosis, liver cirrhosis, and liver cancer. Particularly, when normal hepatocytes were treated with TGFβ, phosphorylation of Smad2/3 was induced along with TM4SF5 expression. In addition, cell/cell contact was lost but α-smooth muscle actin expression was increased, and then EGFR signal transduction system was activated.

Normal liver epithelial cells were treated with the conditioned-medium of LX2 cell line known as the activated hepatic stellate cells (HSC). As a result, the activation of EGFR signal transduction system was induced along with TM4SF5 expression. On the contrary, the expression of TM4SF5 was suppressed by the treatment of EGFR inhibitor. The present inventors constructed a liver disease mouse model demonstrating chronic hepatic injury or hepatic fibrosis by injecting or oral-administering $CCl_4$ or alcohol regularly. It was confirmed by immunohistochemical analysis that TM4SF5 expression was induced according to hepatic injury and inflammation in the mouse model. The region where TM4SF5 was expressed was exactly where TGFβ was expressed and collagen was stained, confirming that TM4SF5 expression was affected by the progress of liver disease such as hepatic fibrosis and liver cirrhosis. It was also confirmed that the compound TSAHC known to counteract the carcinogenic effect of TM4SF5 in liver cancer cells expressing TM4SF5 could inhibit the expression of α-SMA, the marker of EMT, induced by TM4SF5 expression mediated by TGFβ in normal hepatocytes, and at the same time reduced hepatic injury and hepatic fibrosis significantly in the mouse model having liver disease induced by regular injection or oral-administration of $CCl_4$.

Therefore, it was confirmed in this invention that TM4SF5 expression induced by TGFβ over-expressed in liver cancer cells depended on EGFR activation through the interaction between transmembrane receptors in cellular level and TM4SF5 expression was induced over hepatic injury, suggesting that TM4SF5 expression plays an important role in the development of liver disease such as hepatic fibrosis and liver cirrhosis caused by chronic hepatic injury and hepatic inflammation.

The present invention also provides a composition for diagnosing liver disease comprising a material for measuring the expressions and phosphorylations of TM4SF5 expression related signaling proteins by using many proteins involved in TGF-β signal transduction as markers.

For example, the composition for diagnosing liver disease of the present invention can additionally include a material for measuring those proteins up- or down-regulated by EMT (epithelial-mesenchymal transition). Particularly, those proteins up-regulated by EMT are exemplified by α-SMA (α-smooth muscle actin), vimentin, cytoskeleton-intermediate filament, snail, and slug. Those proteins down-regulated by EMT are exemplified by E-adherin, Zo-1 (tight junction protein 1 Zo-1), beta-catenin, desmoplakin, and claudin.

The composition of the present invention can additionally include a material for measuring phosphorylation levels of one or more proteins selected from the group consisting of Smad2 (mothers against decapentaplegic homolog 2), Smad3 (mothers against decapentaplegic homolog 3), EGFR (epidermal growth factor receptor), and Erk1/2 (extracellular signal-regulated kinase 1/2). Herein, the material for measuring phosphorylation levels of the proteins indicates the antibody recognizing specifically those proteins. The antibody herein can be prepared by the conventional technique well-known to those in the art.

The present invention also provides a kit for diagnosing liver disease comprising the said composition for diagnosing liver disease.

The said liver disease is preferably hepatic fibrosis, liver cirrhosis, hepatitis, alcoholic liver disease, or fatty liver, but not always limited thereto.

The diagnostic kit of the present invention can include a material for measuring the grade of TM4SF5 protein, and at this time, the material is preferably the antibody specifically against the protein. Thus, the diagnostic kit comprising a material for measuring the grade of TM4SF5 protein can be, for example, the kit for detecting a diagnostic marker comprising essential elements for ELISA. This kit can contain a reagent for detecting the antibody of "antigen-antibody complex", which is exemplified by labeled secondary antibody, chromophores, enzyme (ex: conjugated with antibody), and substrate thereof. The kit can also include quantification control protein specific antibody.

In addition, the formation of antigen-antibody complex can be quantified by measuring the size of detection label signal. The said detection label can be selected from the group consisting of enzyme, fluorescein, ligand, luminosity, microparticle, redox molecule, and radioisotope, but not always limited thereto. Methods for measuring the protein level is exemplified by Western blotting, ELISA, radioimmunoassay, radioimmunodiffusion, Ouchterlony immunodiffusion, rocket immunoelectrophoresis, immunohistostaining, immunoprecipitation, complement fixation test, FACS, and protein chip assay, but not always limited thereto.

The present invention also provides a method for providing information for diagnosing liver disease comprising the following steps:

1) measuring the grade of TM4SF5 protein in the biological sample separated from a subject with suspected liver disease; and 2) comparing the grade of TM4SF5 protein measured above with that of the normal control sample.

In step 1), the measurement of TM4SF5 protein level in the biological sample separated from a patient having suspected liver disease is preferably performed by contacting the composition for diagnosing liver disease of the present invention with the biological sample, but not always limited thereto.

In step 1), the biological sample is preferably tissue, cell, whole blood, serum, or blood plasma, but not always limited thereto.

The method for detecting TF4SF5 in step 2) is to compare TM4SF5 protein level of the experimental sample with the protein level of the normal control sample to confirm that TM4SF5 level of the experimental sample is higher than that of the control, by which information necessary for diagnosing liver disease can be provided. By comparing TM4SF5 protein level of the normal control with that of a patient having suspected liver disease, the patient can be diagnosed as a liver disease patient or normal and further progress of liver disease or prognosis can also be predicted.

The measurement of the grade of TM4SF5 protein can be performed by using TM4SF5 specific antibody. Particularly, various methods for measuring the protein level such as Western blotting, ELISA, radioimmunoassay, radioimmunodiffusion, Ouchterlony immunodiffusion, rocket immunoelectrophoresis, immunohistostaining, immunoprecipitation, complement fixation test, FACS, and protein chip assay can be used herein.

The present invention also provides a method for screening a material for treating liver disease comprising the following steps:

1) treating candidate materials for treating liver disease to hepatocytes expressing TM4SF5 (Transmembrane 4 L six family member 5 or Four-Transmembrane L6 Superfamily member 5) protein; and 2) selecting the candidate material that is confirmed to inhibit the expression of TM4SF5 protein as the material for treating liver disease, by comparing that of the control group not treated with the candidate materials of step 1).

Herein, the hepatocyte can be any hepatocyte expressing TM4SF5 protein. Particularly, the hepatocyte is preferably the cell expressing the polypeptide represented by SEQ. ID. NO: 2 expressed from the polynucleotide represented by SEQ. ID. NO: 1. The hepatocyte expressing the polypeptide represented by SEQ. ID. NO: 2 is exemplified by SNU449 liver cancer cell line expressing TM4SF5 (KCLB No. 00449), Huh7, and HepG2 cell line. In addition, hepatocytes obtained from chronic hepatic injury, hepatitis, hepatic fibrosis, liver cirrhosis, and fatty liver induced by $CCl_4$ or alcohol, or artificially prepared hepatocytes can also be included herein. The artificially prepared hepatocytes herein indicate the cells expressing TM4SF5 protein which are generated by clone technique including gene manipulation.

In the step of treating candidate materials for treating liver disease to hepatocytes, the candidate materials can be those expected to have liver disease treating activity or those randomly selected among nucleic acids, peptides, proteins, antibodies, extracts or natural substances, and compounds, according to the conventional selection method. Preferably, the candidate material can be the compound inhibiting TM4SF5 protein expression.

According to the method for screening of the present invention, candidate materials for treating liver disease were treated to hepatocytes or tissues or other biological samples, followed by measurement of the grade of TM4SF5 protein and the expression and phosphorylation levels of TM4SF5 expression related signaling proteins to select those materials usable for the treatment or prevention of liver disease. The candidate materials confirmed to inhibit TM4SF5 expression and the expressions and phosphorylations of TM4SF5 expression related signaling proteins were determined as the materials for the treatment and/or prevention of liver disease. In the method for screening of the present invention, reaction among the said materials can be investigated by the conventional methods used for the examination of such reactions as protein-protein, protein-compound, or protein reactions with the said candidate materials such as nucleic acids, peptides, antibodies, other extracts or natural substances.

The present invention also provides a composition for the treatment or prevention of liver disease comprising a material inhibiting TM4SF5 expression or activity.

The present invention also provides a material inhibiting TM4SF5 expression or activity for the preparation of a drug for the treatment or prevention of liver disease.

The present invention also provides a method for treating liver disease containing the step of administering a pharmaceutically effective dose of a material inhibiting TM4SF5 expression or activity to a subject with liver disease.

In addition, the present invention provides a method for preventing liver disease containing the step of administering a pharmaceutically effective dose of a material inhibiting TM4SF5 expression or activity to a subject.

The said TM4SF5 protein is preferably the polypeptide having the amino acid sequence represented by SEQ. ID. NO: 2, but not always limited thereto.

The said liver disease is preferably hepatic fibrosis, liver cirrhosis, hepatitis, alcoholic liver disease, or fatty liver, but not always limited thereto.

The material inhibiting TM4SF5 expression or activity is preferably the sulfonyl-chalcone compound represented by following [Formula 1]~[Formula 4] and [Table 1], but not always limited thereto.

The expressed TM4SF5 protein is functioning to increase α-SMA expression, that is to induce EMT (epithelial-mesenchymal transition) and p27 expression as well as to increase p27 Ser10 phosphorylation, and thus the decrease of TM4SF5 protein activity results in the decrease of α-SMA expression, or EMT (epithelial-mesenchymal transition) reduction, the decrease of p27 expression, and the decrease of p27 Ser 10 phosphorylation level.

That is, the present invention also provides a pharmaceutical composition for the treatment or prevention of liver disease comprising a material inhibiting the expressions and phosphorylations of TM4SF5 expression related signaling proteins by inhibiting TM4SF5 expression or activity.

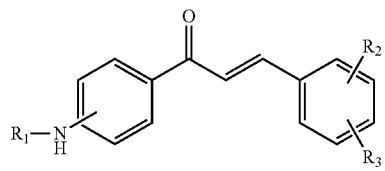

[Formula 1]

Wherein, $R_1$ is $R_4SO_2$—;

$R_2$ and $R_3$ are independently hydrogen or hydroxyl group;

$R_4$ is $C_1$~$C_5$ alkyl; or $C_6$~$C_{10}$ aryl having one or more substituents selected from the group consisting of hydrogen, halogen, nitro, and $C_1$~$C_5$ alkyl, preferably methyl, benzyl, p-toluoyl, p-nitrophenyl, or p-fluorophenyl.

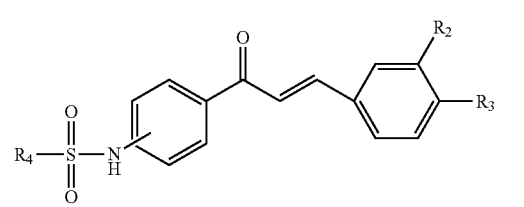

[Formula 2]

Wherein, $R_2$ and $R_3$ are independently hydrogen or hydroxyl group;

$R_4$ is $C_1$~$C_5$ alkyl; or $C_6$~$C_{10}$ aryl having one or more substituents selected from the group consisting of hydrogen, halogen, nitro, and $C_1$~$C_5$ alkyl.

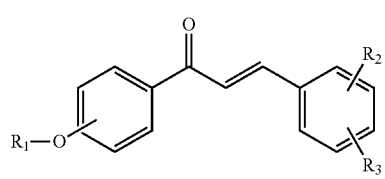

[Formula 3]

Wherein, $R_1$ is $R_4SO_2$—;

$R_2$ and $R_3$ are independently hydrogen or hydroxyl group;

$R_4$ is $C_1$~$C_5$ alkyl; or $C_6$~$C_{10}$ aryl having one or more substituents selected from the group consisting of hydrogen, halogen, nitro, and $C_1$~$C_5$ alkyl, preferably methyl, benzyl, p-toluoyl, p-nitrophenyl, or p-fluorophenyl.

[Formula 4]

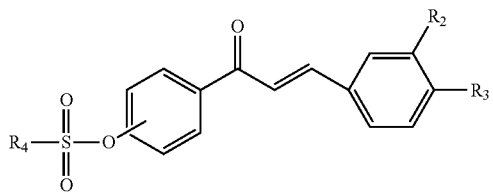

Wherein, $R_2$ and $R_3$ are independently hydrogen or hydroxyl group;

$R_4$ is $C_1$~$C_5$ alkyl; or $C_6$~$C_{10}$ aryl having one or more substituents selected from the group consisting of hydrogen, halogen, nitro, and $C_1$~$C_5$ alkyl.

The material inhibiting TM4SF5 protein expression or activity of the present invention is an anti-liver disease material which is preferably a chalcone compound shown in Table 1. Among those compounds listed in Table 1, TSAHC [4'-(p-toluenesulfonylamino)-4-hydroxy chalcone] represented by compound 1 is the most representative compound.

TABLE 1

| Compound | Structure |
|---|---|
| 1 | 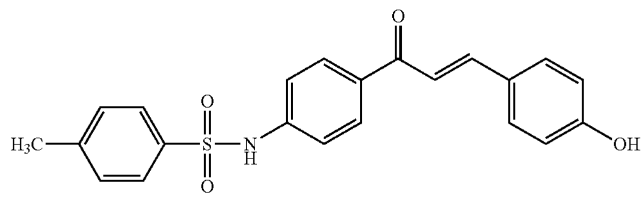 |
| 2 | 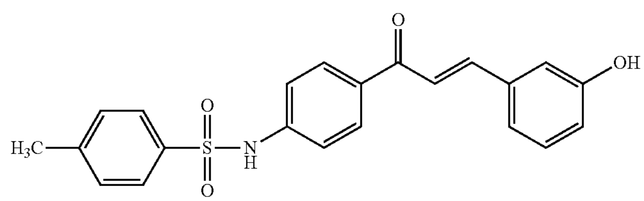 [SMILES: Cc1ccc(S(=O)(=O)Nc2ccc(C(=O)/C=C/c3cccc(O)c3)cc2)cc1] |
| 3 | 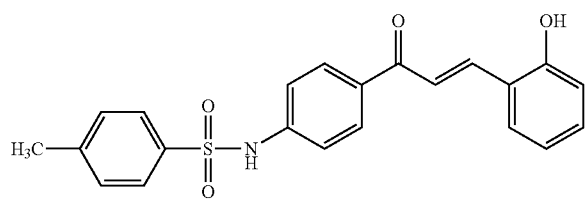 [SMILES: Cc1ccc(S(=O)(=O)Nc2ccc(C(=O)/C=C/c3ccccc3O)cc2)cc1] |
| 4 | 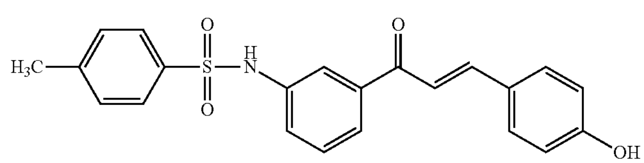 [SMILES: Cc1ccc(S(=O)(=O)Nc2cccc(C(=O)/C=C/c3ccc(O)cc3)c2)cc1] |
| 5 | 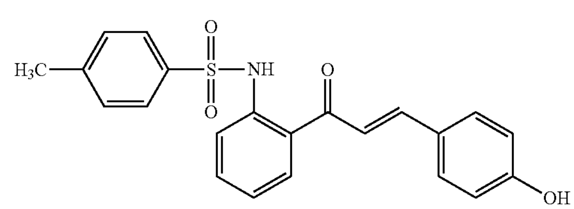 [SMILES: Cc1ccc(S(=O)(=O)Nc2ccccc2C(=O)/C=C/c2ccc(O)cc2)cc1] |
| 6 | 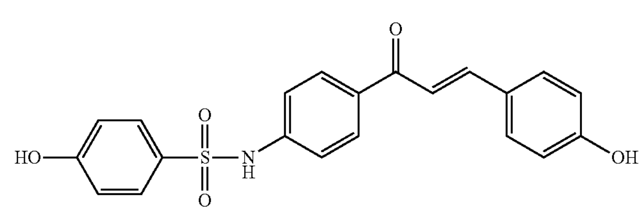 [SMILES: O=C(/C=C/c1ccc(O)cc1)c1ccc(NS(=O)(=O)c2ccc(O)cc2)cc1] |

TABLE 1-continued

| Compound | Structure |
|---|---|
| 7 | 4-hydroxy-N-[4-[(E)-3-(3-hydroxyphenyl)prop-2-enoyl]phenyl]benzenesulfonamide |
| 8 | 4-hydroxy-N-[4-[(E)-3-(2-hydroxyphenyl)prop-2-enoyl]phenyl]benzenesulfonamide |
| 9 | 4-hydroxy-N-[3-[(E)-3-(4-hydroxyphenyl)prop-2-enoyl]phenyl]benzenesulfonamide |
| 10 | 4-hydroxy-N-[3-[(E)-3-(3-hydroxyphenyl)prop-2-enoyl]phenyl]benzenesulfonamide |
| 11 | 4-hydroxy-N-[3-[(E)-3-(2-hydroxyphenyl)prop-2-enoyl]phenyl]benzenesulfonamide |
| 12 | 4-hydroxy-N-[2-[(E)-3-(4-hydroxyphenyl)prop-2-enoyl]phenyl]benzenesulfonamide |
| 13 | 4-hydroxy-N-[2-[(E)-3-(3-hydroxyphenyl)prop-2-enoyl]phenyl]benzenesulfonamide |
| 14 | 4-hydroxy-N-[2-[(E)-3-(2-hydroxyphenyl)prop-2-enoyl]phenyl]benzenesulfonamide |

TABLE 1-continued
| Compound | Structure |
|---|---|
| 15 | 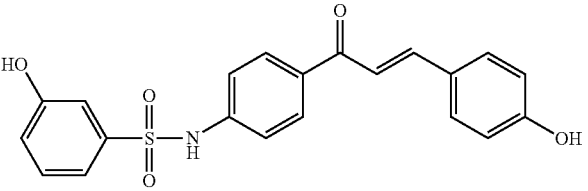 [SMILES: O=C(/C=C/c1ccc(O)cc1)c1ccc(NS(=O)(=O)c2cccc(O)c2)cc1] |
| 16 | 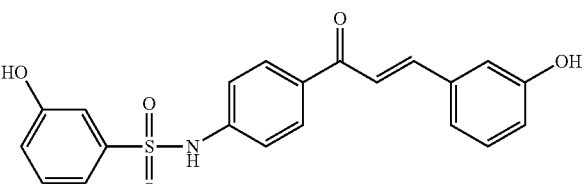 |
| 17 | 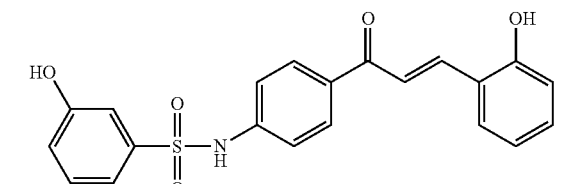 |
| 18 | 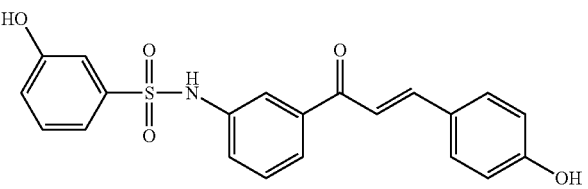 [SMILES: O=C(/C=C/c1ccc(O)cc1)c1cccc(NS(=O)(=O)c2cccc(O)c2)c1] |
| 19 | 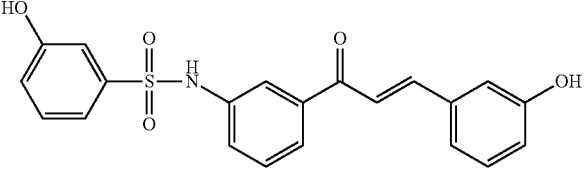 [SMILES: O=C(/C=C/c1cccc(O)c1)c1cccc(NS(=O)(=O)c2cccc(O)c2)c1] |
| 20 | 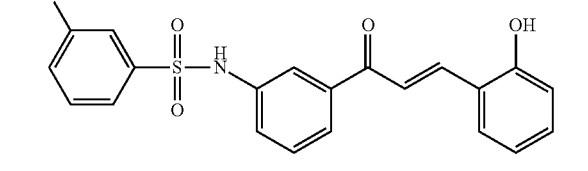 |
| 21 | 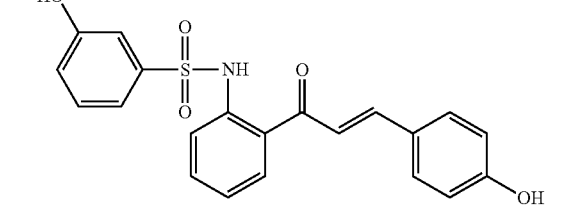 |

TABLE 1-continued

| Compound | Structure |
| --- | --- |
| 22 | 3-hydroxyphenylsulfonamide linked to 2-aminophenyl (E)-3-(3-hydroxyphenyl)prop-2-en-1-one |
| 23 | 3-hydroxyphenylsulfonamide linked to 2-aminophenyl (E)-3-(2-hydroxyphenyl)prop-2-en-1-one |
| 24 | 4-fluorophenylsulfonamide linked to 4-aminophenyl (E)-3-(4-hydroxyphenyl)prop-2-en-1-one |
| 25 | 3-fluorophenylsulfonamide linked to 4-aminophenyl (E)-3-(4-hydroxyphenyl)prop-2-en-1-one |
| 26 | 2-fluorophenylsulfonamide linked to 4-aminophenyl (E)-3-(4-hydroxyphenyl)prop-2-en-1-one |
| 27 | 4-nitrophenylsulfonamide linked to 4-aminophenyl (E)-3-(4-hydroxyphenyl)prop-2-en-1-one |
| 28 | 3-nitrophenylsulfonamide linked to 4-aminophenyl (E)-3-(4-hydroxyphenyl)prop-2-en-1-one |

TABLE 1-continued

| Compound | Structure |
|---|---|
| 29 | 2-nitrobenzenesulfonamide of 4′-amino-4-hydroxychalcone |
| 30 | 4-aminobenzenesulfonamide of 4′-amino-4-hydroxychalcone |
| 31 | 3-aminobenzenesulfonamide of 4′-amino-4-hydroxychalcone |
| 32 | 2-aminobenzenesulfonamide of 4′-amino-4-hydroxychalcone |
| 33 | benzenesulfonamide of 4′-amino-4-hydroxychalcone |
| 34 | methanesulfonamide of 4′-amino-4-hydroxychalcone |
| 35 | 4-methylbenzenesulfonate ester of 4′-hydroxy-4-hydroxychalcone |

TABLE 1-continued

| Compound | Structure |
|---|---|
| 36 | 4-fluorophenylsulfonyl ester of 4'-hydroxy-4-hydroxychalcone |
| 37 | 3-fluorophenylsulfonyl ester of 4'-hydroxy-4-hydroxychalcone |
| 38 | 4-nitrophenylsulfonyl ester of 4'-hydroxy-4-hydroxychalcone |
| 39 | 4-aminophenylsulfonyl ester of 4'-hydroxy-4-hydroxychalcone |
| 40 | phenylsulfonyl ester of 4'-hydroxy-4-hydroxychalcone |
| 41 | methanesulfonyl ester of 4'-hydroxy-4-hydroxychalcone |
| 42 | 4-methylphenylsulfonamide of 4'-amino-3,4-dihydroxychalcone |

TABLE 1-continued
| Compound | Structure |
|---|---|
| 43 | 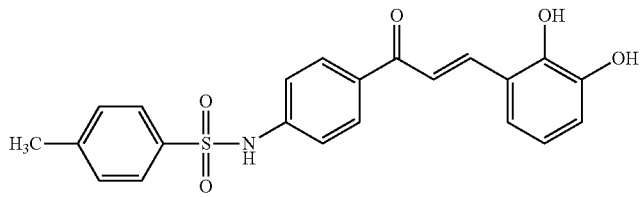 [SMILES: Cc1ccc(S(=O)(=O)Nc2ccc(C(=O)/C=C/c3cccc(O)c3O)cc2)cc1] |
| 44 | 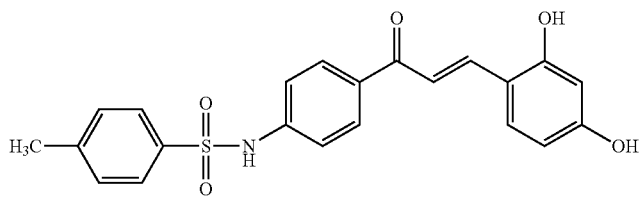 |
| 45 | 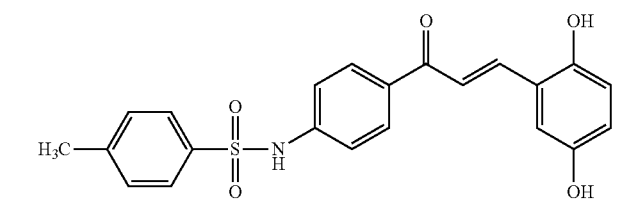 [SMILES: Cc1ccc(S(=O)(=O)Nc2ccc(C(=O)/C=C/c3cc(O)ccc3O)cc2)cc1] |
| 46 | 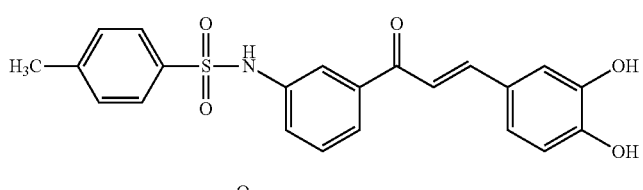 |
| 47 | 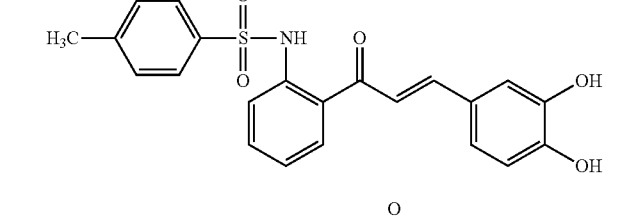 |
| 48 | 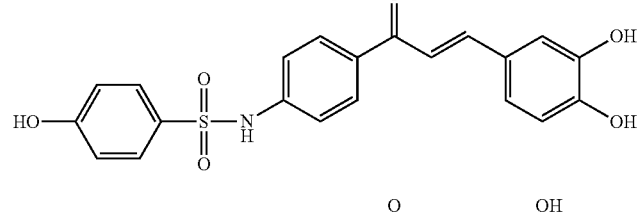 |
| 49 | 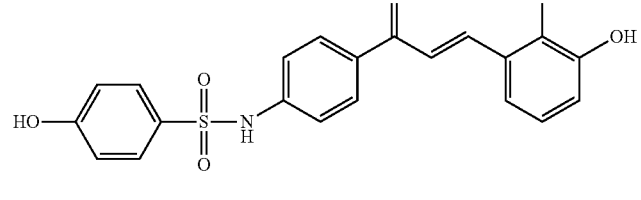 |
| 50 | 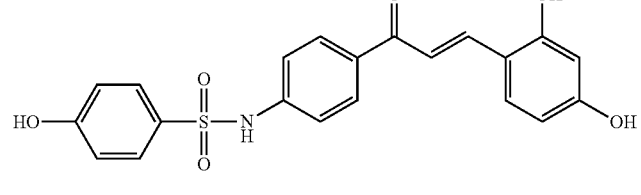 |

TABLE 1-continued

| Compound | Structure |
|---|---|
| 51 | 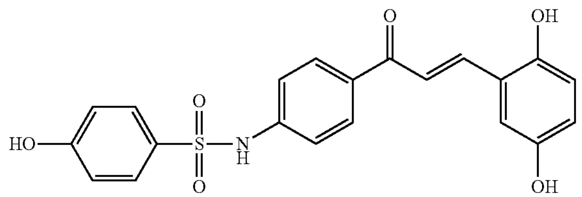 [SMILES: O=C(/C=C/c1cc(O)ccc1O)c1ccc(NS(=O)(=O)c2ccc(O)cc2)cc1] |
| 52 | 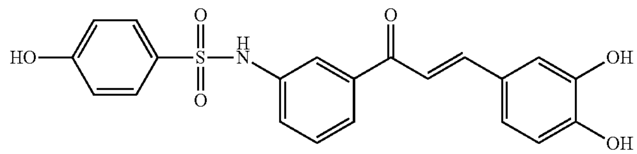 [SMILES: O=C(/C=C/c1ccc(O)c(O)c1)c1cccc(NS(=O)(=O)c2ccc(O)cc2)c1] |
| 53 | 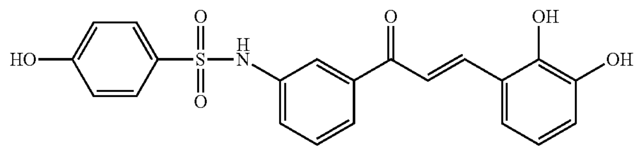 [SMILES: O=C(/C=C/c1cccc(O)c1O)c1cccc(NS(=O)(=O)c2ccc(O)cc2)c1] |
| 54 | 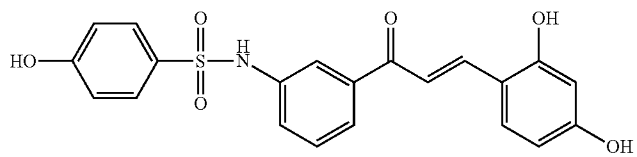 [SMILES: O=C(/C=C/c1ccc(O)cc1O)c1cccc(NS(=O)(=O)c2ccc(O)cc2)c1] |
| 55 | 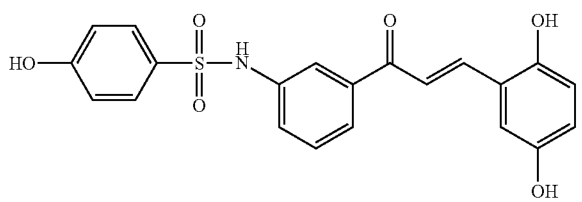 [SMILES: O=C(/C=C/c1cc(O)ccc1O)c1cccc(NS(=O)(=O)c2ccc(O)cc2)c1] |
| 56 | 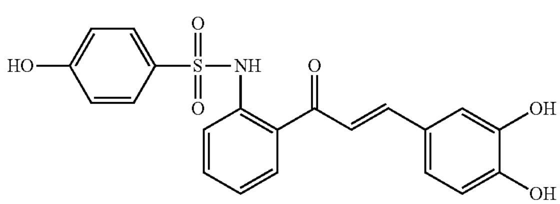 [SMILES: O=C(/C=C/c1ccc(O)c(O)c1)c1ccccc1NS(=O)(=O)c1ccc(O)cc1] |
| 57 | 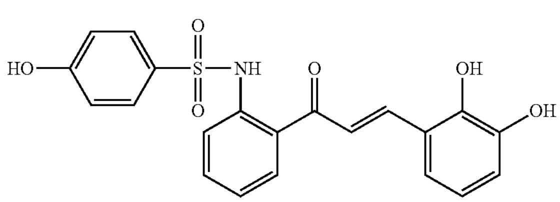 [SMILES: O=C(/C=C/c1cccc(O)c1O)c1ccccc1NS(=O)(=O)c1ccc(O)cc1] |
| 58 | 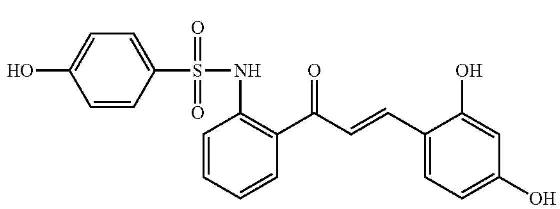 [SMILES: O=C(/C=C/c1ccc(O)cc1O)c1ccccc1NS(=O)(=O)c1ccc(O)cc1] |

TABLE 1-continued

| Compound | Structure |
|---|---|
| 59 | 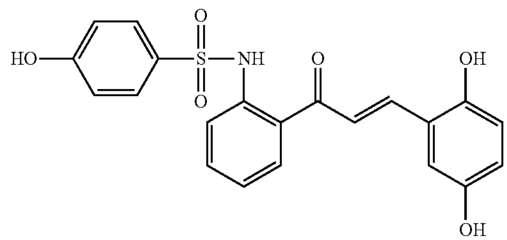 [SMILES: O=C(/C=C/c1cc(O)ccc1O)c1ccccc1NS(=O)(=O)c1ccc(O)cc1] |
| 60 | 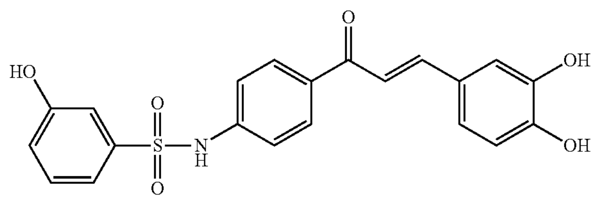 [SMILES: O=C(/C=C/c1ccc(O)c(O)c1)c1ccc(NS(=O)(=O)c2cccc(O)c2)cc1] |
| 61 | 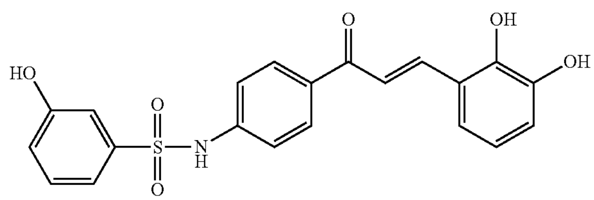 [SMILES: O=C(/C=C/c1cccc(O)c1O)c1ccc(NS(=O)(=O)c2cccc(O)c2)cc1] |
| 62 | 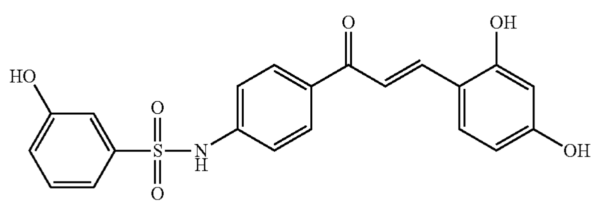 |
| 63 | 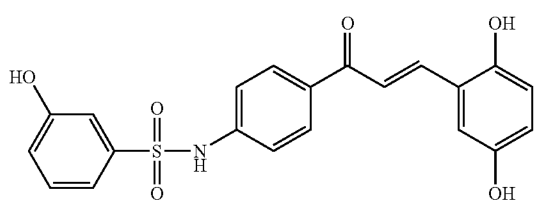 [SMILES: O=C(/C=C/c1cc(O)ccc1O)c1ccc(NS(=O)(=O)c2cccc(O)c2)cc1] |
| 64 | 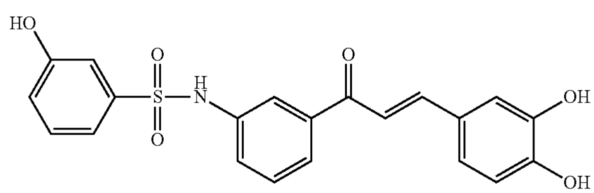 [SMILES: O=C(/C=C/c1ccc(O)c(O)c1)c1cccc(NS(=O)(=O)c2cccc(O)c2)c1] |
| 65 | 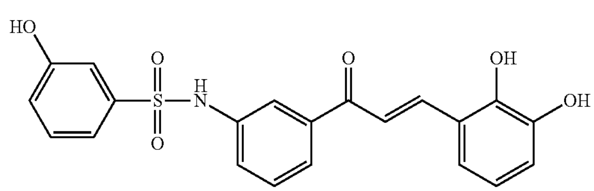 [SMILES: O=C(/C=C/c1cccc(O)c1O)c1cccc(NS(=O)(=O)c2cccc(O)c2)c1] |

TABLE 1-continued

| Compound | Structure |
|---|---|
| 66 | 3-hydroxyphenylsulfonamide linked to 3-aminophenyl chalcone with 2,4-dihydroxyphenyl |
| 67 | 3-hydroxyphenylsulfonamide linked to 3-aminophenyl chalcone with 2,5-dihydroxyphenyl |
| 68 | 3-hydroxyphenylsulfonamide linked to 2-aminophenyl chalcone with 3,4-dihydroxyphenyl |
| 69 | 3-hydroxyphenylsulfonamide linked to 2-aminophenyl chalcone with 2,3-dihydroxyphenyl |
| 70 | 3-hydroxyphenylsulfonamide linked to 2-aminophenyl chalcone with 2,4-dihydroxyphenyl |
| 71 | 3-hydroxyphenylsulfonamide linked to 2-aminophenyl chalcone with 2,5-dihydroxyphenyl |
| 72 | 4-fluorophenylsulfonamide linked to 4-aminophenyl chalcone with 3,4-dihydroxyphenyl |

TABLE 1-continued

| Compound | Structure |
|---|---|
| 73 | 3-fluorobenzenesulfonamide of 4'-amino-3,4-dihydroxychalcone |
| 74 | 2-fluorobenzenesulfonamide of 4'-amino-3,4-dihydroxychalcone |
| 75 | 4-nitrobenzenesulfonamide of 4'-amino-3,4-dihydroxychalcone |
| 76 | 3-nitrobenzenesulfonamide of 4'-amino-3,4-dihydroxychalcone |
| 77 | 2-nitrobenzenesulfonamide of 4'-amino-3,4-dihydroxychalcone |
| 78 | 4-aminobenzenesulfonamide of 4'-amino-3,4-dihydroxychalcone |
| 79 | 3-aminobenzenesulfonamide of 4'-amino-3,4-dihydroxychalcone |

TABLE 1-continued

| Compound | Structure |
|---|---|
| 80 | 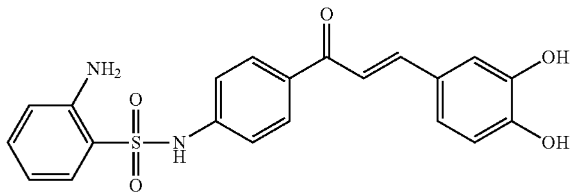 [SMILES: Nc1ccccc1S(=O)(=O)Nc1ccc(C(=O)/C=C/c2ccc(O)c(O)c2)cc1] |
| 81 | 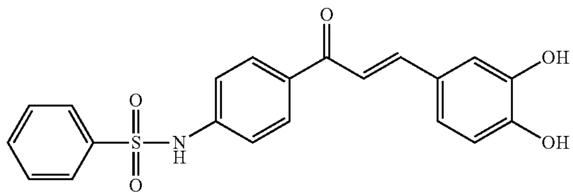 [SMILES: O=C(/C=C/c1ccc(O)c(O)c1)c1ccc(NS(=O)(=O)c2ccccc2)cc1] |
| 82 | 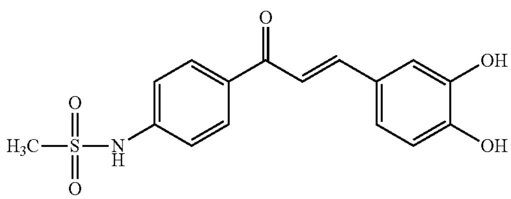 [SMILES: CS(=O)(=O)Nc1ccc(C(=O)/C=C/c2ccc(O)c(O)c2)cc1] |
| 83 | 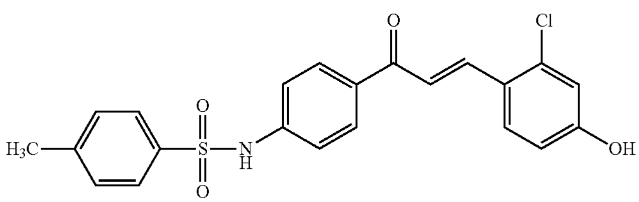 [SMILES: Cc1ccc(S(=O)(=O)Nc2ccc(C(=O)/C=C/c3ccc(O)cc3Cl)cc2)cc1] |
| 84 | 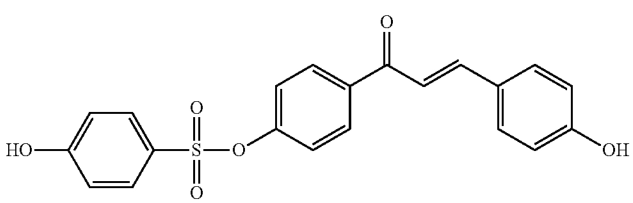 [SMILES: O=C(/C=C/c1ccc(O)cc1)c1ccc(OS(=O)(=O)c2ccc(O)cc2)cc1] |
| 85 | 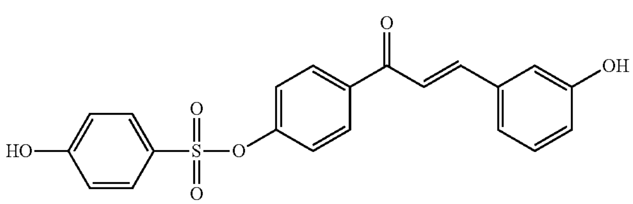 [SMILES: O=C(/C=C/c1cccc(O)c1)c1ccc(OS(=O)(=O)c2ccc(O)cc2)cc1] |
| 86 | 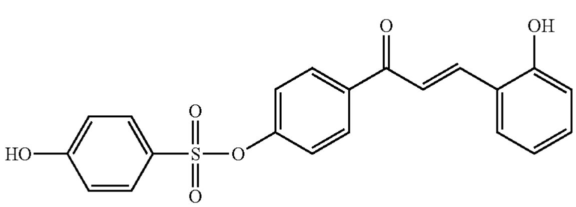 |

TABLE 1-continued

| Compound | Structure |
|---|---|
| 87 | 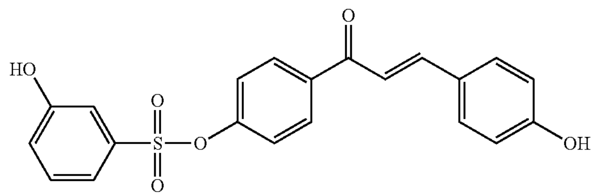 [SMILES: O=C(/C=C/c1ccc(O)cc1)c1ccc(OS(=O)(=O)c2cccc(O)c2)cc1] |
| 88 | 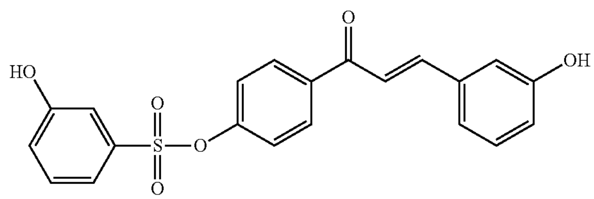 [SMILES: O=C(/C=C/c1cccc(O)c1)c1ccc(OS(=O)(=O)c2cccc(O)c2)cc1] |
| 89 | 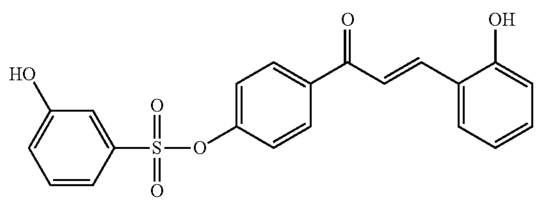 [SMILES: O=C(/C=C/c1ccccc1O)c1ccc(OS(=O)(=O)c2cccc(O)c2)cc1] |
| 90 | 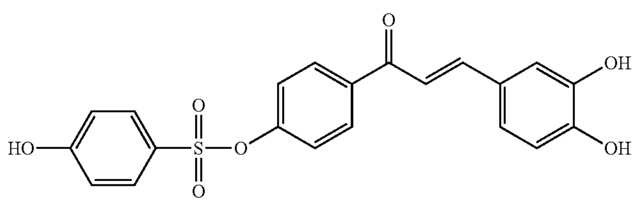 [SMILES: O=C(/C=C/c1ccc(O)c(O)c1)c1ccc(OS(=O)(=O)c2ccc(O)cc2)cc1] |
| 91 | 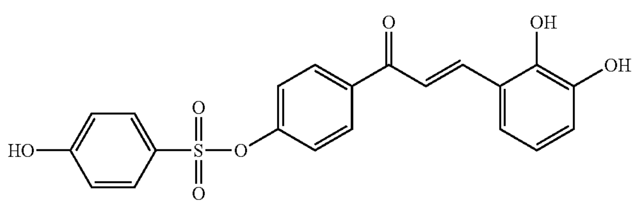 [SMILES: O=C(/C=C/c1cccc(O)c1O)c1ccc(OS(=O)(=O)c2ccc(O)cc2)cc1] |
| 92 | 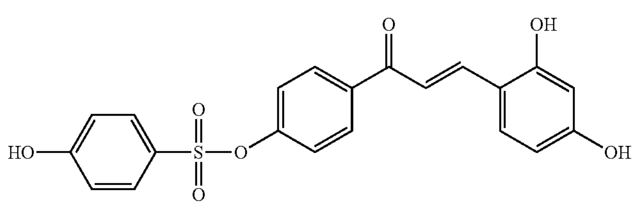 [SMILES: O=C(/C=C/c1ccc(O)cc1O)c1ccc(OS(=O)(=O)c2ccc(O)cc2)cc1] |
| 93 | 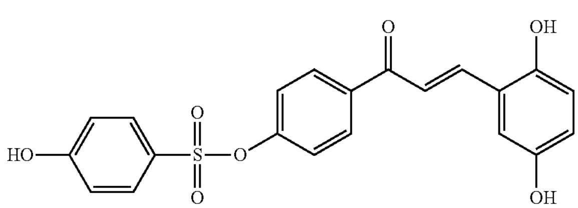 [SMILES: O=C(/C=C/c1cc(O)ccc1O)c1ccc(OS(=O)(=O)c2ccc(O)cc2)cc1] |

TABLE 1-continued

| Compound | Structure |
|---|---|
| 94 | (structure) |
| 95 | (structure) |
| 96 | (structure) |
| 97 | (structure) |

Compound 1~compound 97 presented in Table 1 are as follows.
4'-(p-toluenesulfonylamino)-4-hydroxychalcone;
4'-(p-toluenesulfonylamino)-3-hydroxychalcone;
4'-(p-toluenesulfonylamino)-2-hydroxychalcone;
3'-(p-toluenesulfonylamino)-4-hydroxychalcone;
2'-(p-toluenesulfonylamino)-4-hydroxychalcone;
4'-(p-hydroxybenzenesulfonylamino)-4-hydroxychalcone;
4'-(p-hydroxybenzenesulfonylamino)-3-hydroxychalcone;
4'-(p-hydroxybenzenesulfonylamino)-2-hydroxychalcone;
3'-(p-hydroxybenzenesulfonylamino)-4-hydroxychalcone;
3'-(p-hydroxybenzenesulfonylamino)-3-hydroxychalcone;
3'-(p-hydroxybenzenesulfonylamino)-2-hydroxychalcone;
2'-(p-hydroxybenzenesulfonylamino)-4-hydroxychalcone;
2'-(p-hydroxybenzenesulfonylamino)-3-hydroxychalcone;
2'-(p-hydroxybenzenesulfonylamino)-2-hydroxychalcone;
4'-(m-hydroxybenzenesulfonylamino)-4-hydroxychalcone;
4'-(m-hydroxybenzenesulfonylamino)-3-hydroxychalcone;
4'-(m-hydroxybenzenesulfonylamino)-2-hydroxychalcone;
3'-(m-hydroxybenzenesulfonylamino)-4-hydroxychalcone;
3'-(m-hydroxybenzenesulfonylamino)-3-hydroxychalcone;
3'-(m-hydroxybenzenesulfonylamino)-2-hydroxychalcone;
2'-(m-hydroxybenzenesulfonylamino)-4-hydroxychalcone;
2'-(m-hydroxybenzenesulfonylamino)-3-hydroxychalcone;
2'-(m-hydroxybenzenesulfonylamino)-2-hydroxychalcone;
4'-(p-fluorobenzenesulfonylamino)-4-hydroxychalcone;
4'-(m-fluorobenzenesulfonylamino)-4-hydroxychalcone;
4'-(o-fluorobenzenesulfonylamino)-4-hydroxychalcone;
4'-(p-nitrobenzenesulfonylamino)-4-hydroxychalcone;
4'-(m-nitrobenzenesulfonylamino)-4-hydroxychalcone;
4'-(o-nitrobenzenesulfonylamino)-4-hydroxychalcone;
4'-(p-aminobenzenesulfonylamino)-4-hydroxychalcone;
4'-(m-aminobenzenesulfonylamino)-4-hydroxychalcone;
4'-(o-aminobenzenesulfonylamino)-4-hydroxychalcone;
4'-(benzenesulfonylamino)-4-hydroxychalcone;
4'-(methanesulfonylamino)-4-hydroxychalcone;
4'-(p-toluenesulfonate)-4-hydroxychalcone;
4'-(p-fluorobenzenesulfonate)-4-hydroxychalcone;
4'-(m-fluorobenzenesulfonate)-4-hydroxychalcone;
4'-(p-nitrobenzenesulfonate)-4-hydroxychalcone;
4'-(p-aminobenzenesulfonate)-4-hydroxychalcone;
4'-(benzenesulfonate)-4-hydroxychalcone;
4'-(methanesulfonate)-4-hydroxychalcone;
4'-(p-toluenesulfonylamino)-3,4-dihydroxychalcone;
4'-(p-toluenesulfonylamino)-2,3-dihydroxychalcone;
4'-(p-toluenesulfonylamino)-2,4-dihydroxychalcone;
4'-(p-toluenesulfonylamino)-2,5-dihydroxychalcone;
3'-(p-toluenesulfonylamino)-3,4-dihydroxychalcone;
2'-(p-toluenesulfonylamino)-3,4-dihydroxychalcone;
4'-(p-hydroxybenzenesulfonylamino)-3,4-dihydroxychalcone;
4'-(p-hydroxybenzenesulfonylamino)-2,3-dihydroxychalcone;
4'-(p-hydroxybenzenesulfonylamino)-2,4-dihydroxychalcone;
4'-(p-hydroxybenzenesulfonylamino)-2,5-dihydroxychalcone;
3'-(p-hydroxybenzenesulfonylamino)-3,4-dihydroxychalcone;

3'-(p-hydroxybenzenesulfonylamino)-2,3-dihydroxychalcone;
3'-(p-hydroxybenzenesulfonylamino)-2,4-dihydroxychalcone;
3'-(p-hydroxybenzenesulfonylamino)-2,5-dihydroxychalcone;
2'-(p-hydroxybenzenesulfonylamino)-3,4-dihydroxychalcone;
2'-(p-hydroxybenzenesulfonylamino)-2,3-dihydroxychalcone;
2'-(p-hydroxybenzenesulfonylamino)-2,4-dihydroxychalcone;
2'-(p-hydroxybenzenesulfonylamino)-2,5-dihydroxychalcone;
4'-(m-hydroxybenzenesulfonylamino)-3,4-dihydroxychalcone;
4'-(m-hydroxybenzenesulfonylamino)-2,3-dihydroxychalcone;
4'-(m-hydroxybenzenesulfonylamino)-2,4-dihydroxychalcone;
4'-(m-hydroxybenzenesulfonylamino)-2,5-dihydroxychalcone;
3'-(m-hydroxybenzenesulfonylamino)-3,4-dihydroxychalcone;
3'-(m-hydroxybenzenesulfonylamino)-2,3-dihydroxychalcone;
3'-(m-hydroxybenzenesulfonylamino)-2,4-dihydroxychalcone;
3'-(m-hydroxybenzenesulfonylamino)-2,5-dihydroxychalcone;
2'-(m-hydroxybenzenesulfonylamino)-3,4-dihydroxychalcone;
2'-(m-hydroxybenzenesulfonylamino)-2,3-dihydroxychalcone;
2'-(m-hydroxybenzenesulfonylamino)-2,4-dihydroxychalcone;
2'-(m-hydroxybenzenesulfonylamino)-2,5-dihydroxychalcone;
4'-(p-fluorobenzenesulfonylamino)-3,4-dihydroxychalcone;
4'-(m-fluorobenzenesulfonylamino)-3,4-dihydroxychalcone;
4'-(o-fluorobenzenesulfonylamino)-3,4-dihydroxychalcone;
4'-(p-nitrobenzenesulfonylamino)-3,4-dihydroxychalcone;
4'-(m-nitrobenzenesulfonylamino)-3,4-dihydroxychalcone;
4'-(o-nitrobenzenesulfonylamino)-3,4-dihydroxychalcone;
4'-(p-aminobenzenesulfonylamino)-3,4-dihydroxychalcone;
4'-(m-aminobenzenesulfonylamino)-3,4-dihydroxychalcone;
4'-(o-aminobenzenesulfonylamino)-3,4-dihydroxychalcone;
4'-(benzenesulfonylamino)-3,4-dihydroxychalcone;
4'-(methanesulfonylamino)-3,4-dihydroxychalcone;
4'-(p-toluenebenzenesulfonylamino)-2-chloro-4-hydroxychalcone;
4'-(p-hydroxybenzenesulfonate)-4-hydroxychalcone;
4'-(p-hydroxybenzenesulfonate)-3-hydroxychalcone;
4'-(p-hydroxybenzenesulfonate)-2-hydroxychalcone;
4'-(m-hydroxybenzenesulfonate)-4-hydroxychalcone;
4'-(m-hydroxybenzenesulfonate)-3-hydroxychalcone;
4'-(m-hydroxybenzenesulfonate)-2-hydroxychalcone;
4'-(p-hydroxybenzenesulfonate)-3,4-dihydroxychalcone;
4'-(p-hydroxybenzenesulfonate)-2,3-dihydroxychalcone;
4'-(p-hydroxybenzenesulfonate)-2,4-dihydroxychalcone;
4'-(p-hydroxybenzenesulfonate)-2,5-dihydroxychalcone;
4'-(m-hydroxybenzenesulfonate)-3,4-dihydroxychalcone;
4'-(m-hydroxybenzenesulfonate)-2,3-dihydroxychalcone;
4'-(m-hydroxybenzenesulfonate)-2,4-dihydroxychalcone; and
4'-(m-hydroxybenzenesulfonate)-2,5-dihydroxychalcone.

Korean Publicized Patent No. 10-2003-0036993 describes that chalcone compounds have an activity of inhibiting matrix metalloproteinase (MMP) activity decomposing basement membrane components. However, it does not describe whether or not chalcone compounds are functioning to prevent or treat liver disease. The chalcone compounds represented by Formula 1~Formula 4 of the present invention are characterized by containing sulfone group ($SO_3$—) or sulfoneamide group ($SO_2NH$—) in their structures. The anti-liver activity (function) of chalcone compounds against TM4SF5 is attributed to the sulfone group ($SO_3$—).

In a preferred embodiment of the present invention, TSAHC [4'-(p-toluenesulfonylamino)-4-hydroxy chalcone] (compound 1 of Table 1), one of the representative chalcone compounds, was confirmed to decrease EMT and collagen synthesis and accumulation in hepatocytes, which were inevitable in hepatic injury and hepatic fibrosis induced by $CCl_4$ in mice. Therefore, it was confirmed that the compound can be used for the suppression, treatment, or prevention of liver disease.

The said chalcone compounds are acting as antagonists to inhibit TM4SF5 mediated phenomena specifically.

As described in Korean Patent No. 10-0934706, when one or more chalcone compounds including TSAHC were treated to the cell line expressing TM4SF5, the growth curve was reduced as the concentration of the chalcone compounds increased and as the treatment time was longer. In addition, cell cycle was going back to S phase and cell-cell contact began again by the treatment of the chalcone compounds. However, the chalcone compounds of the present invention did not show any pharmaceutical effect in the cell line not-expressing TM4SF5. It was also investigated whether the chalcone compounds changed the expressions of $p27^{kip1}$, $pS^{10}p27^{kip1}$ and $pY^{577}FAK$, and the expressions of mesenchymal cell marker α-SMA and vimentin. As a result, the expressions of the above were all effectively reduced by the chalcone compounds, by which EMT (epithelial to mesenchymal transition) was inhibited as well. When the chalcone compounds of the present invention were treated to SNU447Tp, the SNU449 cell line expressing TM4SF5, $p27^{kip1}$ existing in cytoplasm could not be stabilized and rather reduced.

The chalcone compounds of the present invention can be used in the forms of chalcone derivatives which are the forms of pharmaceutically acceptable salts.

As for the pharmaceutically acceptable salt, it is preferably an acid addition salt prepared by using a pharmaceutically acceptable free acid. Whether it is inorganic or organic, a free acid can be used if it is pharmaceutically acceptable. Examples of the inorganic free acid include hydrochloric acid, bromic acid, sulfuric acid, and phosphoric acid. Available organic free acids are exemplified by citric acid, acetic acid, lactic acid, malic acid, fumaric acid, gluconic acid, methanesulfonic acid, acetic acid, glycolic acid, succinic acid, tartaric acid, 4-toluenesulfonic acid, galacturonic acid, embonic acid, glutamic acid, and aspartic acid.

The chalcone derivative of the present invention includes not only pharmaceutically acceptable salts but also solvates and hydrates possibly produced from the same.

For the clinical use, the chalcone compound or salt thereof of the present invention can be administered independently, but also can be administered in the form of pharmaceutically formulated mixture prepared by mixing excipients, binding agents, slip modifiers, disintegrating agents, coating agents, emulsifiers, suspending agents, solvents, stabilizers, absorption enhancers, and/or ointment bases with the said compound or the salt. The mixture herein can be used for oral administration, injection, rectal administration or external administration.

As explained hereinbefore, the composition for treating or preventing liver disease that comprises the chalcone compound or salts thereof can be administered orally, for which it can be formulated in the forms of tablets, coated tablets, dragees, hard or soft gelatin capsules, solutions, emulsions, or suspensions. The composition can also be administered to rectum, for which the composition can be formulated as suppositories. The composition can also be administered locally or transdermally in the forms of ointments, creams, gels, or solutions, or the composition can be administered parenterally by injection, for which the composition can be prepared as injectable solutions.

To make the composition in the forms of tablets, coated tablets, dragees, and hard gelatin capsules, the chalcone compound of the present invention can be mixed with a pharmaceutically inactive inorganic or organic excipient (pharmaceutically acceptable carrier). The excipient suitable for making tablets, coated tablets, dragees, and hard or soft gelatin capsules is exemplified by lactose, maize starch or derivatives thereof, and talc or stearic acid or salts thereof. The excipient suitable for making soft gelatin capsules is exemplified by vegetable oil, wax, fat, semi-solid, or liquid polyol. Some soft gelatin capsules might not need any excipient, though, according to the characteristics of their active ingredients. The excipient suitable for making the composition in the forms of solution and syrup is exemplified by water, polyol, saccharose, invert sugar, and glucose. The excipient suitable for making the composition in the forms of injectable solutions is exemplified by water, alcohol, polyol, glycerin, and vegetable oil. The excipient suitable for making the composition in the forms of suppositories and preparations for local or transdermal administration is exemplified by natural oil or hardened oil, wax, fat, and semi-solid or liquid polyol.

The composition for treating or preventing liver disease can additionally include preservatives, resolvents, stabilizers, wetting agents, emulsifiers, sweetening agents, pigments, flavoring agents, osmosis controlling salts, buffering agents, coating agents, or antioxidants. The composition can also include other therapeutically valuable additives.

The pharmaceutical formulation for oral administration can be granule, tablet, sugar-coated tablet, capsule, pill, suspension, or emulsion. In the meantime, the pharmaceutical formulation for parenteral administration (intravenous, intramuscular, or subcutaneous administration) can be sterilized solution. To prepare isotonic solution, the sterilized solution can additionally include other materials such as salts or glucose. The composition of the present invention can also be administered as suppository or pessary and can be applied externally as lotion, solution, cream, ointment, or dusting powder.

Daily dosage of the chalcone compound of the present invention is preferably 5~2,000 mg when it is administered orally or parenterally. The administration frequency is preferably once or at least twice a day. However, the dosage can be adjusted by considering various factors such as administration pathway, patient's age, gender and weight, and severity of disease, etc. Therefore, the preferable dosage cannot limit the scope of the invention in any way.

By the administration of the composition of the present invention, not only liver diseases such as hepatitis, hepatic fibrosis, liver cirrhosis, and fatty liver, but also symptoms or complications induced by those diseases can be treated and prevented.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Confirmation of TM4SF5 Expression and EMT Induced by TGFβ

To investigate the interaction between TGFβ signal transduction system and TM4SF5 protein, the extracts were obtained from normal liver tissues and liver cancer tissues by the following method.

Normal liver tissues and liver cancer tissues were obtained from patients at Kyungpook National University Hospital, Korea in March~April, 2007. The obtained liver tissues were stored in liquid nitrogen. The frozen tissues were pulverized using a homogenizer, which were then extracted by using lysis buffer containing 0.1% SDS (Sigma).

Western blotting was performed with antibodies specifically binding to Smad2/3 and TM4SF5, the TGFβ signal transduction system, to investigate the expression and phosphorylation levels of those proteins. As a result, TM4SF5 was over-expressed and TGFβ signaling Smad2/3 phosphorylation was increased in liver cancer tissues (FIG. 1). Therefore, it was confirmed that TM4SF5 expression and TGFβ were correlated.

EMT in hepatic stellate cells (HSC) and liver epithelial cells was also investigated. To examine whether or not TGFβ known to play a key role in the early stage of liver disease would induce the expression of TM4SF5 which has been known to be over-expressed in liver cancer tissues, luciferase reporter gene assay was performed with TM4SF5 promoter.

Figure 2:
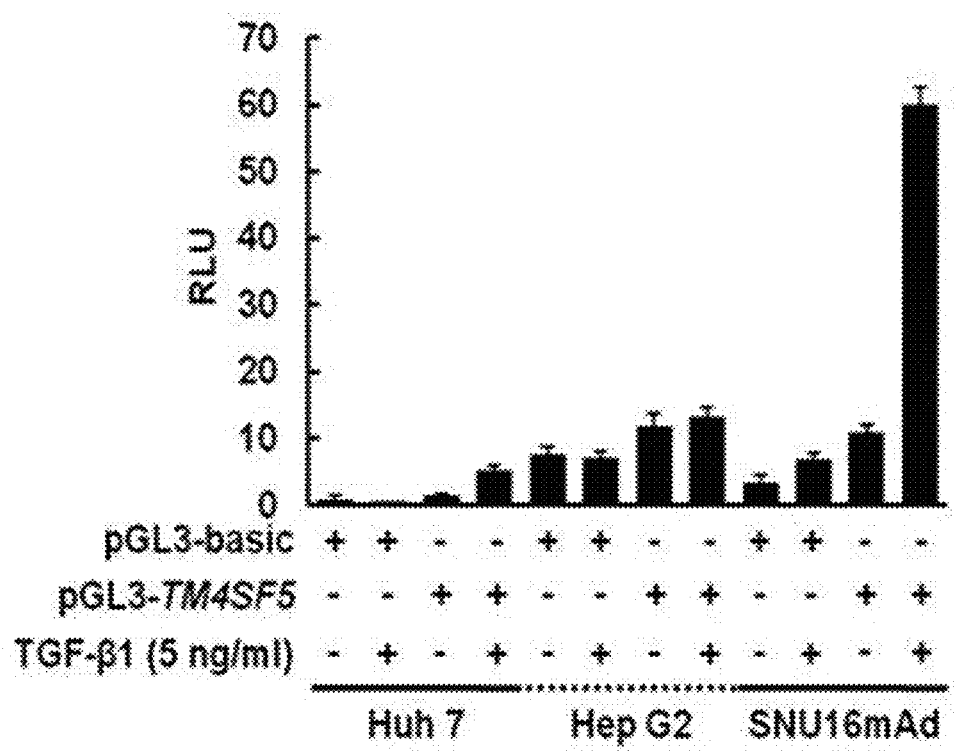

Particularly, Huh7 and HepG2 (liver cancer cell lines), and SNU16mAd (stomach cancer cell line) were transfected with pBabe-galactosidase (Choi et al., 2009, Blood 113:1845-1855) containing pGL3-human TM4SF5 promoter prepared by inserting genomic fragment of TM4SF5 upstream promoter located approximately −3 kb ahead of TM4SF5 gene in pGL3 luciferase vector (Promega), followed by harvesting 24 hours later. Then, luciferase activity of the reporter gene was measured. Infection efficiency was confirmed by measuring beta-galactosidase activity, followed by quantification after normalization. As a result, transcriptional activity of TM4SF5 promoter region was increased by TGFβ, suggesting that TM4SF5 transcription was activated. Unlike pGL3-TM4SF5 that was the construct harboring TM4SF5 promoter region whose transcriptional activity could be confirmed, pGL3-basic was the construct without the promoter, meaning transcription would not be activated, which was thereby used as the control (FIG. 2).

AML12 cells (ATCC, USA), the normal mouse hepatocytes, and Chang cells (ATCC, USA), the normal human hepatocytes, cultured in DMEM supplemented with 10% FBS were washed with serum-free DMEM, which were maintained as serum-free status for 4 hours. After serum starvation, the cells were treated with TGFβ (2.5 ng/ml), followed by further culture for 24 hours. At last, cell extracts were prepared.

TM4SF5 protein expression was increased in those extracts, confirmed by immunoblotting and immunofluorescence assay using antibodies against pSmad3, pSmad2 (Cell Signaling Technology, Danvers, Mass.), vimentin (Sigma-Aldrich), E-adherin (Santa Cruz Biotechnology, Santa Cruz, Calif.), and TM4SF5 (Sin-Ae Lee et al., J. Clin. Invest. 2008 April; 118(4):1354-66). The nucleotide sequence of TM4SF5 antibody was confirmed by using pGEX-5X2 vector (Amersham) comprising c-terminal of TM4SF5 (the region from the $229^{th}$ nucleotide residue to the $594^{th}$ nucleotide residue, digested with EcoR1). To obtain recombinant protein induced by IPTG from DH5a bacteria, PBS comprising 0.3% SDS and protease inhibitor was used. After protein extraction, antigen was extracted from electrophoresed SDS gel, followed by immunizing mice with that. After immune response was induced three times in total, serum was obtained from the mice. Immunoreactivity of the serum with recombinant protein and animal cell extract was investigated.

Figure 3:
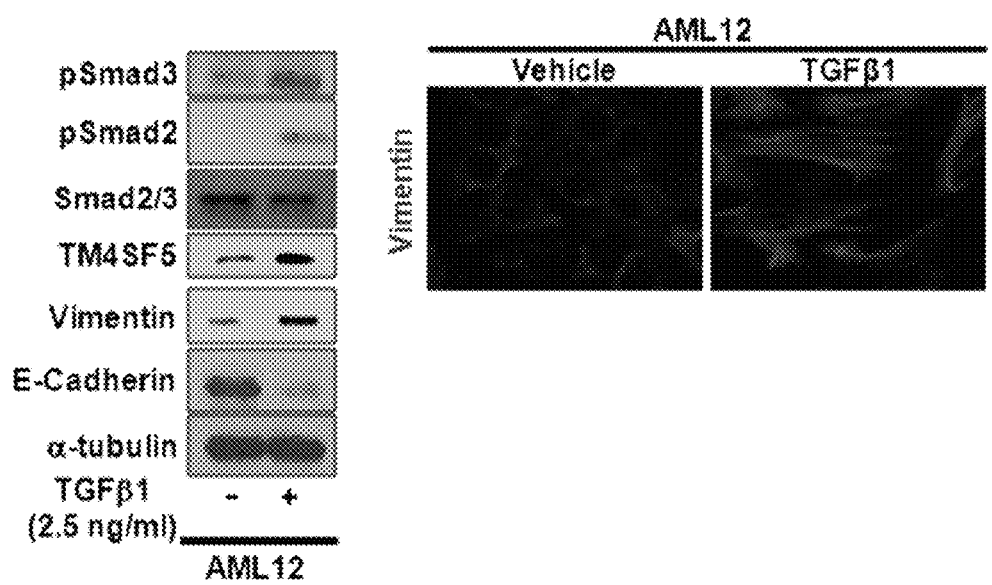
Figure 5:
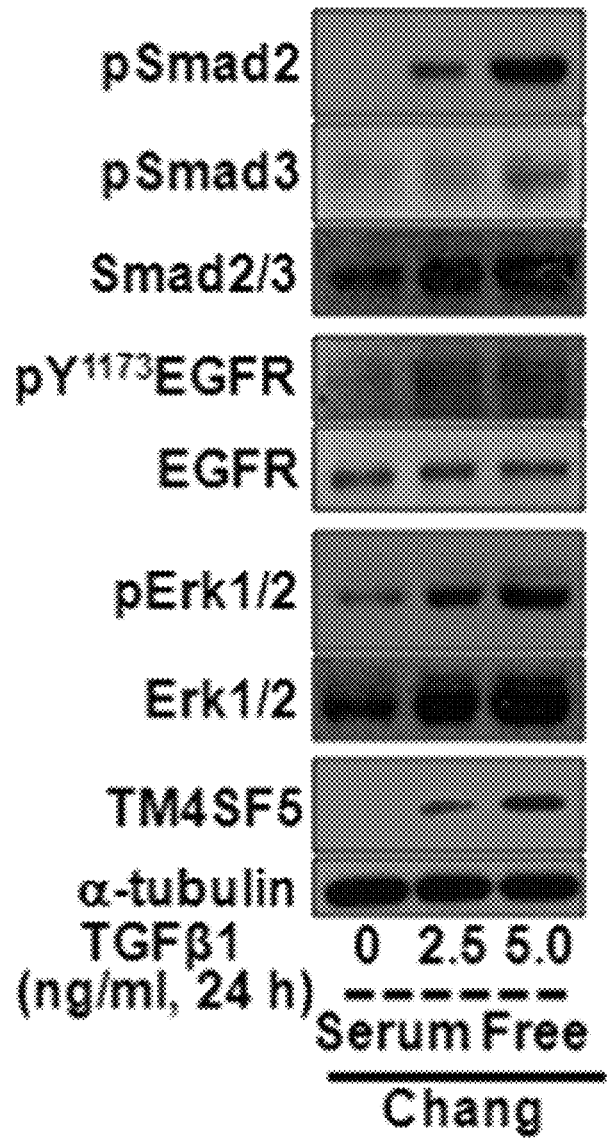
FIG. 5 is a set of photographs illustrating the results of Western blotting performed to confirm the increase of TM4SF5 expression along with the increase of phosphorylation levels of Smad2/3, EGFR Tyr1173, and Erk1/2 in Chang cells over the treatment of TGFβ at different concentrations.

As a result, as shown in FIG. 3 and FIG. 5, when AML12 cells were treated with TGFβ, TM4SF5 expression was increased. In addition, EMT (epithelial-mesenchymal transition) was induced by the increases of α-SMA and vimentin and the decrease of E-cadherin. It was also confirmed by immunoblotting that the expression of E-cadherin, which is important for cell-cell contact, was reduced, but the expression of vimentin, the mesenchymal cell marker, was increased. In the meantime, according to immunofluorescence assay, the cells were placed on cover glass coated with fibronectin (10 μg/ml) to perform immunofluorescence staining, followed by treating with TGFβ. Upon completion of immunofluorescence staining with vimentin antibody, the cover glass was observed under fluorescence microscope. As a result, vimentin expression was increased, compared with the control treated with vehicle (PBS, phosphate saline buffer) only without TGFβ, and EMT was confirmed by dispersed cell pattern (FIG. 3).

Figure 4:
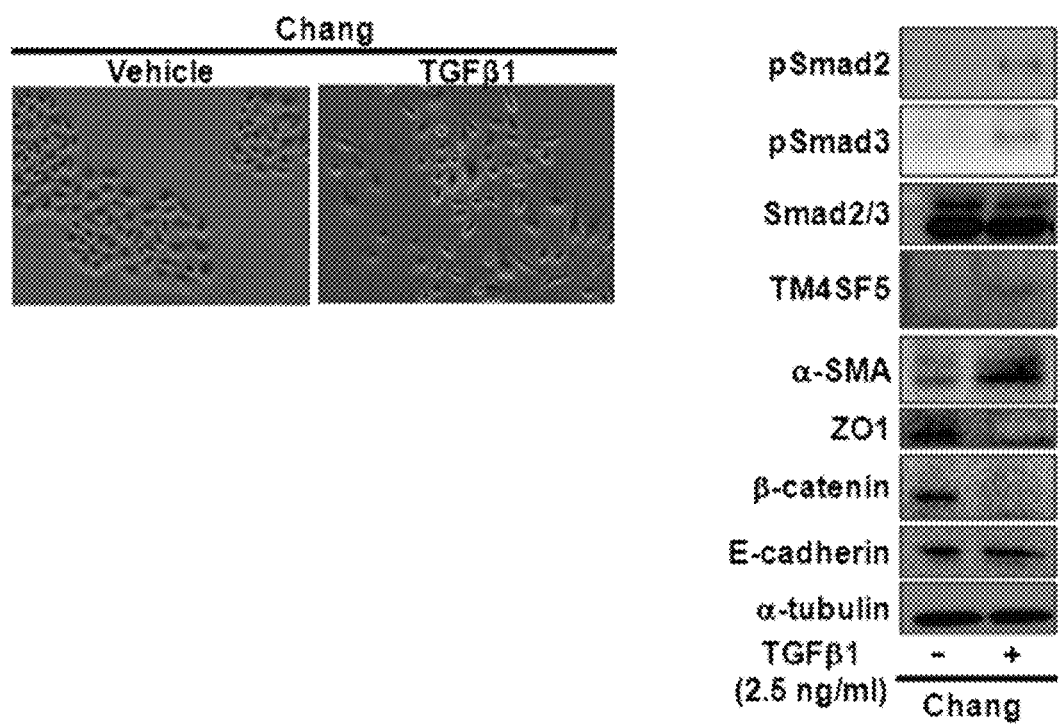

Chang cells, the normal human hepatocytes, were treated with TGFβ, followed by immunoblotting. As a result, it was confirmed that TM4SF5 expression was induced. From the comparison of cellular morphology, it was also confirmed that cell-cell contact became weak, compared with the control treated with vehicle (PBS) only without TGFβ, and EMT was induced, and the expression of α-SMA, the mesenchymal cell marker, was increased (FIG. 4).

In addition, Chang cells, the normal human hepatocytes, were treated with TGFβ at different concentrations of 0, 2.5 and 5 ng/ml, followed by immunoblotting. As a result, it was confirmed that the expression of TM4SF5 protein was increased TGFβ dose-dependently. EGFR signal transduction system was also activated, confirmed by using antibodies against phospho-$Y^{1173}$EGFR (Santa Cruz Biotechnology, Santa Cruz, Calif.), EGFR (Santa Cruz Biotechnology, Santa Cruz, Calif.), phospho-Erk, phospho-Smad2, phospho-Smad3 (Cell Signaling Technology, Danvers, Mass.), and α-tubulin (Sigma-Aldrich) (FIG. 5).

Example 2

Confirmation of TM4SF5 Expression Induced by Conditioned-Medium of Hepatic Stellate Cells Hepatic stellate cells in the liver are activated by the stimulus like TGFβ, and the activated hepatic stellate cells secrete various cytokines that affect neighboring liver epithelial cells. ALM12 cells were treated with conditioned medium of LX2 cells (Dr. Scott Friedman, Mount Sinai School of Medicine, NY), the activated hepatic stellate cells, followed by investigation of the effect on AML12 cells.

The conditioned medium is the medium in which LX2 cells, the hepatic stellate cells, were cultured for 12 or 24 hours in the presence of 0.2% FBS. AML12 cells were treated with the conditioned medium. 24 hours later, TM4SF5 expression was examined by Western blotting. The protein in the lysate extracted from the cells was quantified and the same amount of the protein was used each time. For Western blotting, 8~12% SDS gel, and antibodies against phospho-$Y^{1173}$EGFR (Santa Cruz Biotechnology, Santa Cruz, Calif.), phospho-$Y^{992}$EGFR (Cell Signaling Technology, Danvers, Mass.), EGFR (Santa Cruz Biotechnology, Santa Cruz, Calif.), phospho-Erk, phospho-Smad2, phospho-Smad3 (Cell Signaling Technology, Danvers, Mass.), TM4SF5, and α-tubulin (Sigma-Aldrich) were used.

Figure 6:
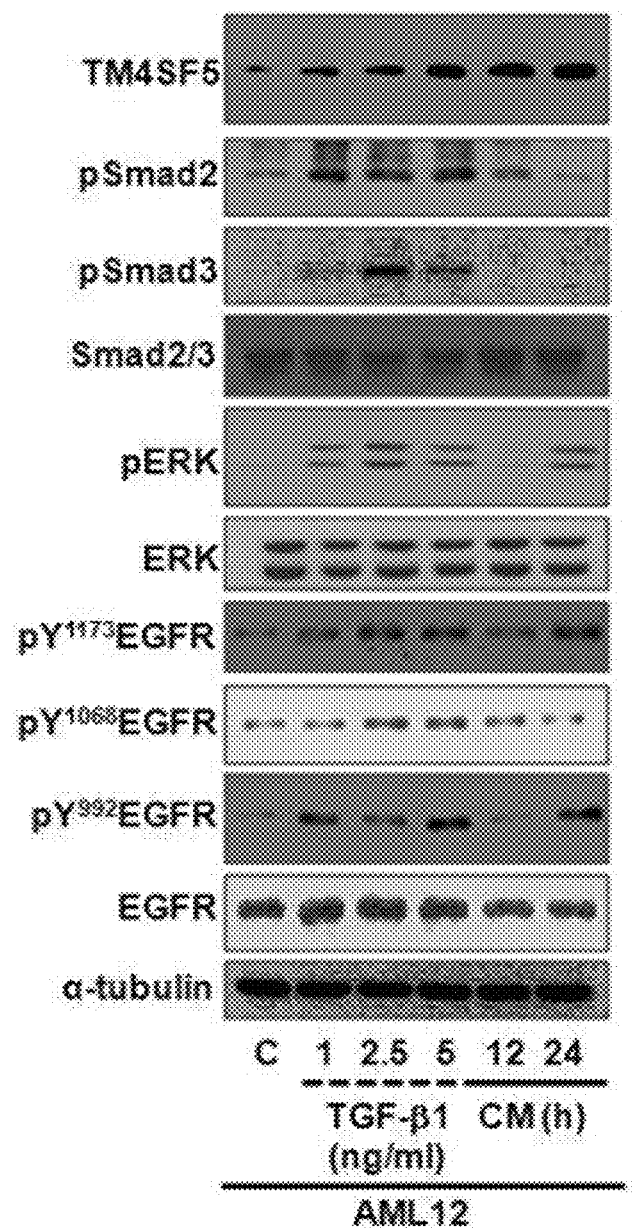
FIG. 6 is a set of photographs illustrating the results of Western blotting performed to confirm the increase of TM4SF5 expression in AML12 cells after the treatment of TGFβ at different concentrations and the treatment of the conditioned-medium of LX2 cells known as activated hepatic stellate cells for 12 hours and 24 hours.

As a result, it was confirmed that TM4SF5 expression in AML12 cells was increased by the treatment of the conditioned medium of LX2 cells. Such TM4SF5 up-regulation was accompanied by EGFR/Erk activation, suggesting that EGFR signal transduction system was activated at the same time (FIG. 6).

Example 3

Confirmation of Involvement of EGFR Signal Transduction System in TM4SF5 Expression Induced by TGFβ

(1) To investigate the role of EGFR signal transduction system in TM4SF5 expression induced by TGFβ, AG1478, the EGFR inhibitor, was used.

Particularly, AML12 cells were cultured in DMEM supplemented with 10% FBS, which were then washed with serum-free DMEM. The cells were maintained as serum-free status for 4 hours. After serum starvation, the cells were treated with DMSO (control vehicle) and AG1478 (100 nM) 30 minutes before the treatment of TGFβ (2.5 ng/ml) in order to inhibit EGFR signaling. After the treatment of TGFβ (R&D systems, Minneapolis, Minn., USA), the cells were further cultured for 24 more hours.

Western blotting was performed with antibodies against phospho-$Y^{1173}$EGFR (Santa Cruz Biotechnology, Santa Cruz, Calif.), phospho-$Y^{992}$EGFR (Cell Signaling Technology, Danvers, Mass.), phospho-Erk (Cell Signaling Technology, Danvers, Mass.), phospho-Smad2 (Cell Signaling Technology, Danvers, Mass.), phospho-Smad3 (Cell Signaling Technology, Danvers, Mass.), TM4SF5, and α-tubulin (Sigma-Aldrich) to investigate the expressions of TM4SF5 and EGFR signal transduction system related factors.

Figure 7:
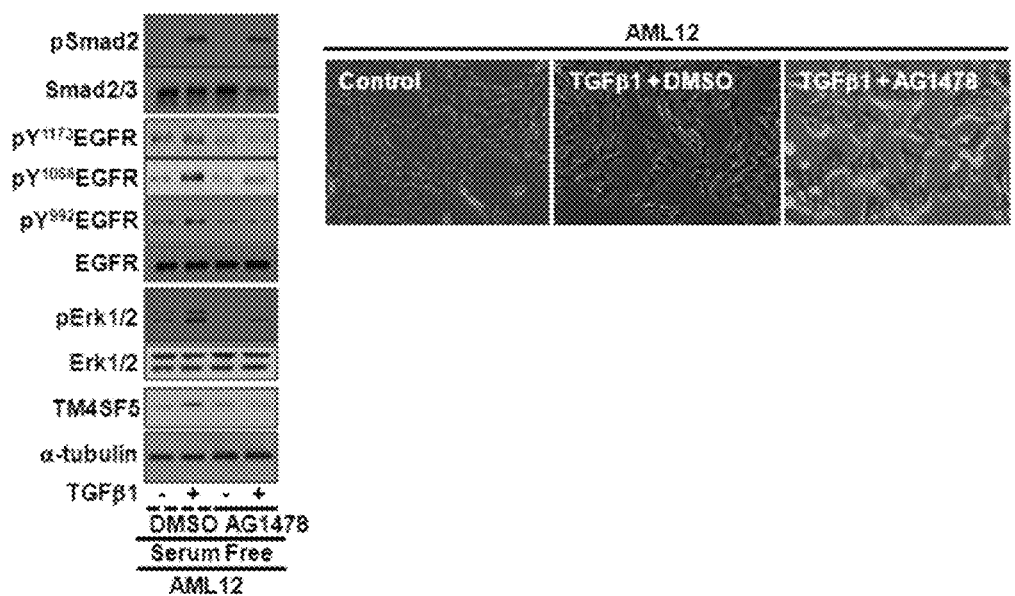
FIG. 7 is a set of photographs illustrating that the expression of TM4SF5 and the cell morphology change induced by the treatment of TGFβ in AML12 cells are suppressed by the treatment of AG1478, the EGFR inhibitor.

As a result, as shown in FIG. 7, it was confirmed that TGFβ mediated TM4SF5 expression was decreased in the group treated with AG1478. It was also confirmed by optical microscope observation that cell-cell contact was eliminated by the treatment of TGFβ, indicating EMT. When AG1478 (LC Laboratories, Woburn, Mass., USA), the EGFR inhibitor, was treated, cell-cell contact was maintained, suggesting that TGFβ mediated cell dispersion was inhibited by AG1478.

Therefore, it was confirmed that TM4SF5 expression induced by TGFβ was inhibited by EGFR inhibitor, suggesting that EGFR activation is necessary for inducing TGFβ mediated TM4SF5 expression.

Figure 8:
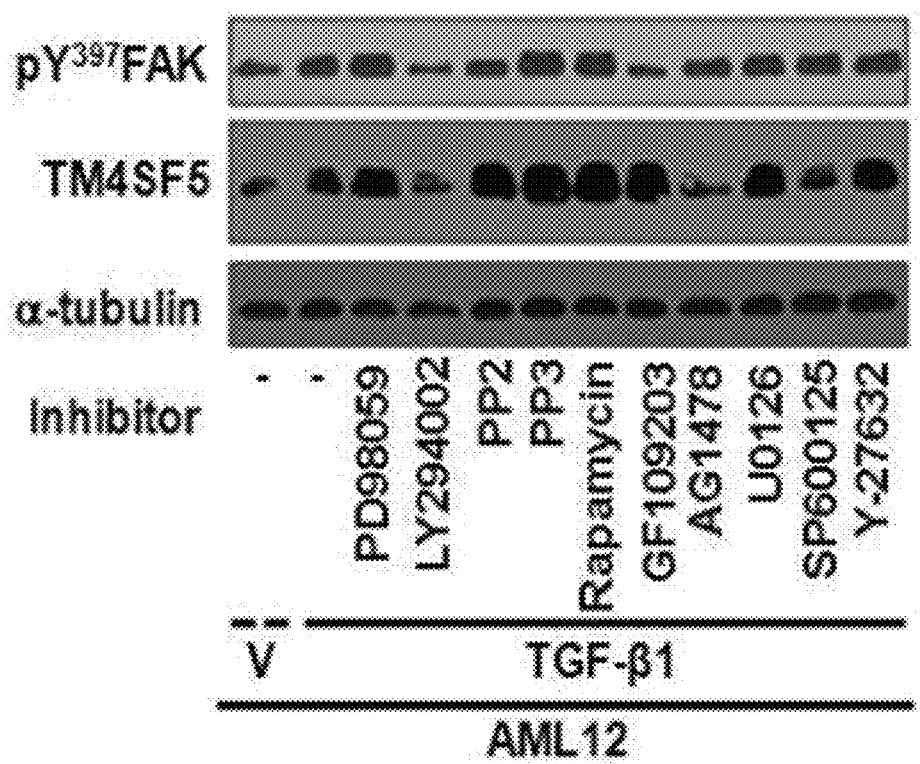
FIG. 8 is a set of photographs illustrating the results of Western blotting performed to confirm TM4SF5 expressions over the treatment of different inhibitors in AML12 cells.

(2) AML12 cells were cultured in DMEM supplemented with 10% FBS, which were then washed with serum-free DMEM. The cells were maintained as serum-free status for 4 hours. After serum starvation, the cells were treated with various inhibitors such as PD98059 (MEK inhibitor, LC Laboratories, Woburn, Mass.), LY294002 (PI3K inhibitor), PP2, PP3 (src inhibitor, Tocris Cookson, Avonmouth, UK), Rapamycin (mTOR inhibitor), GF109203 (PKC inhibitor, Calbiochem, San Diego, Calif.), AG1478 (EGFR inhibitor, LC Laboratories, Woburn, Mass.), U0126 (ERK1/2 inhibitor, LC Laboratories, Woburn, Mass.), SP600125 (Jnk inhibitor), and Y-27632 (ROCK inhibitor, Calbiochem, San Diego, Calif.) 30 minutes before the treatment of TGFβ (2.5 ng/ml). Then, TM4SF5 expression was examined. As a result, TM4SF5 expression was reduced by AG1478 under the near death condition (the condition in which phospho-$Y^{397}$ FAK level was high) (FIG. 8).

(3) In the induction of TGFβ mediated TM4SF5 expression, EGF was treated to the cells along with TGFβ, followed by the investigation of their roles in TM4SF5 expression.

Figure 9:
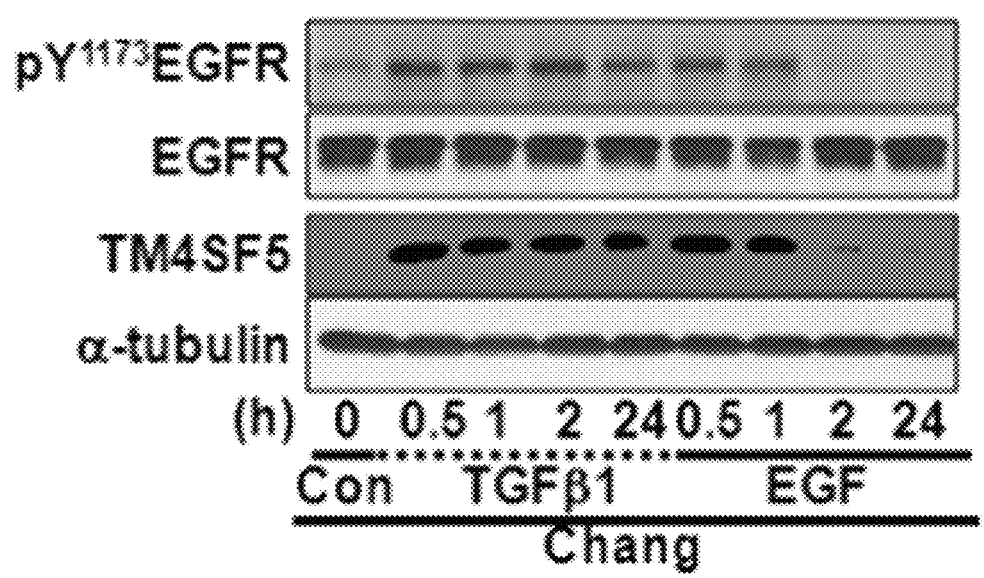
FIG. 9 is a set of photographs illustrating the results of Western blotting performed to confirm the increases of TM4SF5 expression and phospho-$Y^{1173}$ EGFR over the treatment times of TGFβ and EGF in Chang cells.
Figure 10:
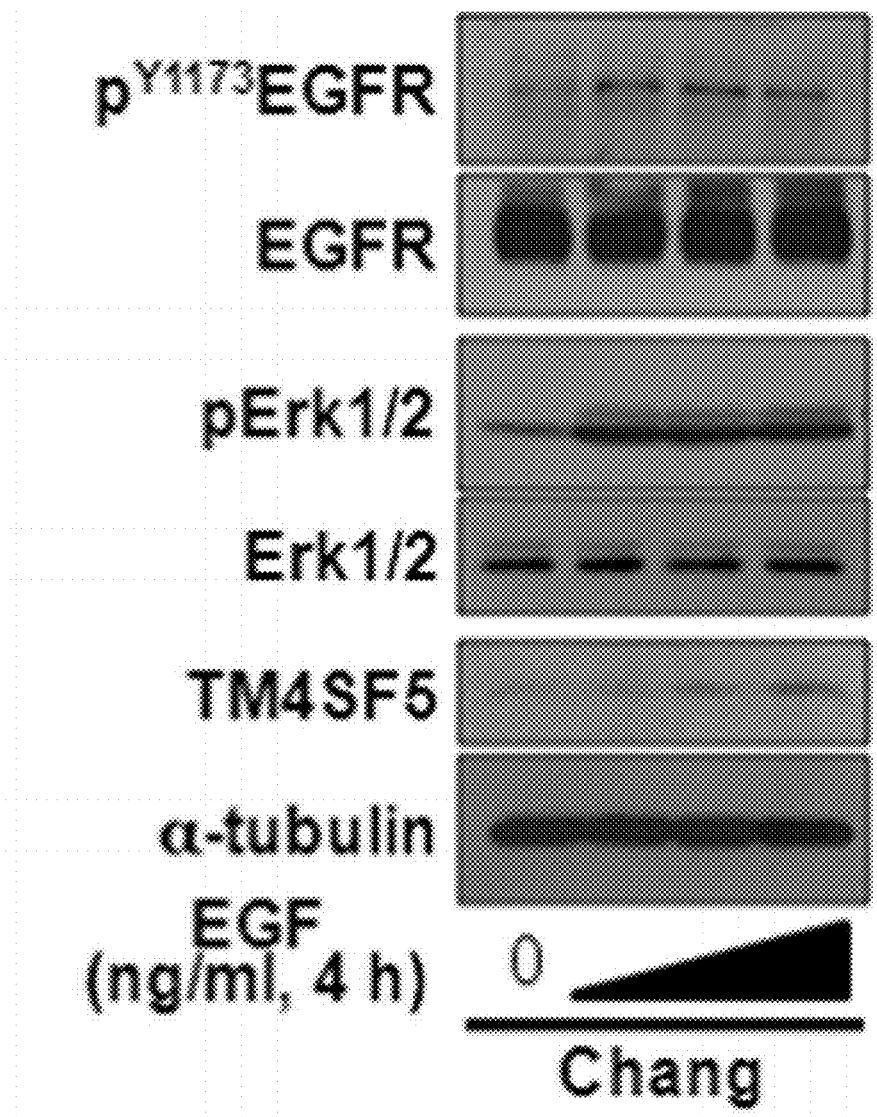
FIG. 10 is a set of photographs illustrating the results of Western blotting performed to confirm the increases of TM4SF5 expression, phospho-$Y^{1173}$ EGFR, and phospho-Erk1/2 over the treatment of EGF at different concentrations for 4 hours.

Chang cells were cultured in DMEM supplemented with 10% FBS, which were then washed with serum-free DMEM. The cells were maintained as serum-free status for 4 hours. After serum starvation, the cells were treated with TGFβ (2.5 ng/ml) and EGF (50 ng/ml), followed by culture for 0, 0.5, 1, 2, and 24 hours. Then, TM4SF5 expression and EGFR signal transduction system were investigated. In the group treated with TGFβ, EGFR signal transduction system activation and TM4SF5 expression were induced continuously up to 24 hours from 30 minutes from the treatment. In the group treated with EGF, EGFR signal transduction system activation and TM4SF5 expression were induced temporally (FIG. 9). In the group treated with EGF only for 4 hours at different concentrations, EGFR signal transduction system activation and TM4SF5 expression were not particularly induced by EGF alone (FIG. 10). Therefore, it was suggested that the continuous activation of EGFR signal transduction system mediated by TGFβ played a key role in inducing TM4SF5 expression.

(4) In the induction of TGFβ mediated TM4SF5 expression, it was investigated whether or not TM4SF5 expression was increased by the direct activation of EGFR signal transduction system by the treatment of growth factor such as EGF.

AML12 cells were cultured in DMEM supplemented with 10% FBS, which were then washed with serum-free DMEM. The cells were maintained as serum-free status for 4 hours. After serum starvation, the cells were treated with EGF, HGF, and PDGF (PeproTech, Inc., Rocky Hill, N.J., USA) 30 minutes before the treatment of TGFβ (2.5 ng/ml) in order to activate EGFR signaling. The cells were further cultured for 24 hours after the treatment of TGFβ. AML12 cell line was the normal hepatocyte cell line which was sensitive to serum. To make near death condition, the medium was regulated as serum-free and the experiment was carried out under the serum-free condition and ITS (Insulin, transferrin, selenium, Sigma-Aldrich) treated condition, which was the same serum-free condition as mentioned above.

Figure 11:
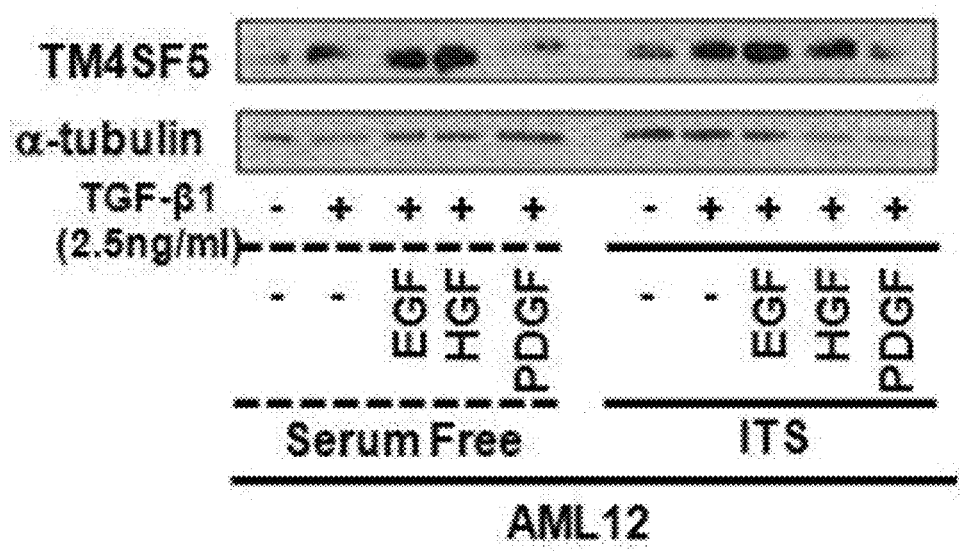
FIG. 11 is a set of photographs illustrating the results of Western blotting performed to confirm the increase of TM4SF5 expression over the treatments of TGFβ, EGF, HGF, and PDGF in AML12 cells.

Western blotting was performed to confirm TM4SF5 expression. As a result, when the cells were treated with EGF, HGF, and PDGF, EGFR signaling was activated and thereby TM4SF5 expression was increased (FIG. 11). Therefore, it was suggested that EGFR signal transduction system played a crucial role in inducing TGFβ mediated TM4SF5 expression.

(5) In the induction of TM4SF5 expression mediated by conditioned medium of LX2 cells, the hepatic stellate cells, it was investigated whether or not EGFR signal transduction system activation was involved in TM4SF5 expression by using AG1478.

Particularly, one hour before the treatment of conditioned medium of LX2 cells to AML12 cells, AG1478 (100 nM) was added to the medium to inhibit EGFR kinase activity, leading to the suppression of EGFR signaling, which was then treated to AML12 cells, followed by further culture for 24 hours.

Figure 12:
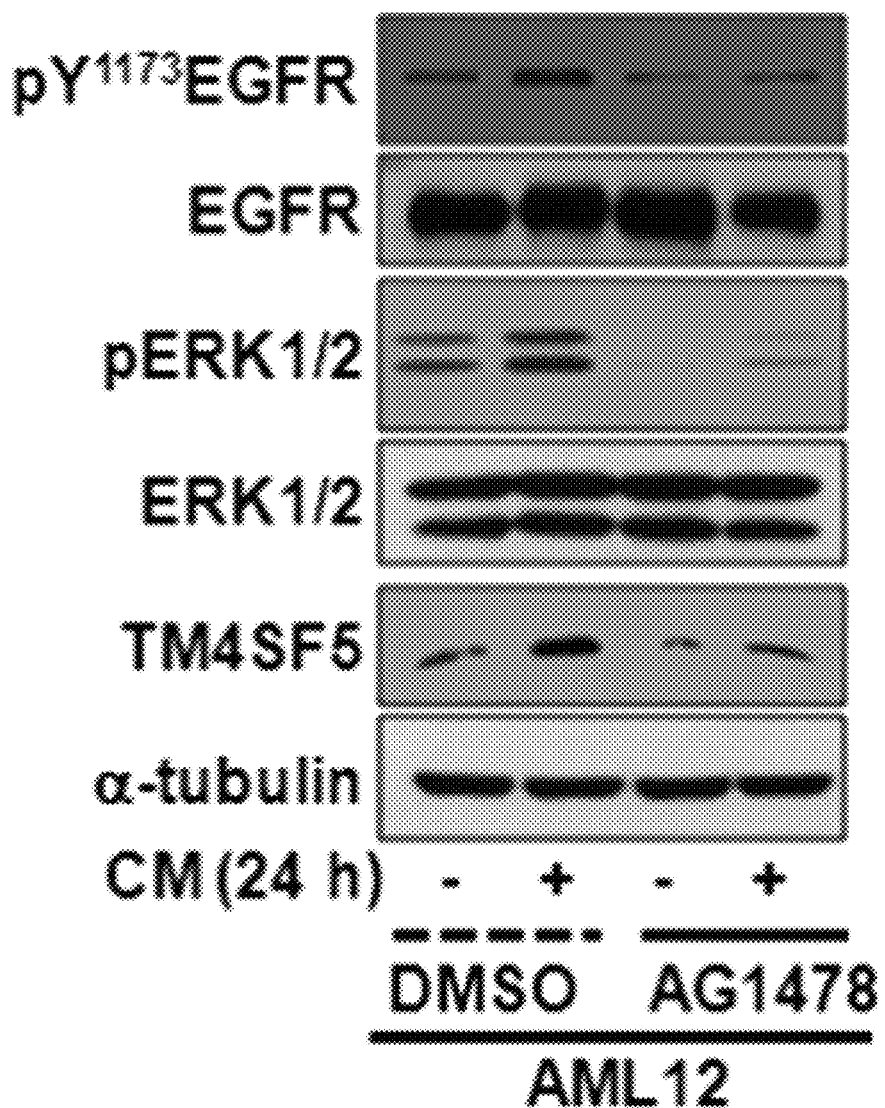
FIG. 12 is a set of photographs illustrating the results of Western blotting performed to confirm that TM4SF5 expression up-regulated by the treatment of conditioned-medium in AML12 cells was not increased any more by the treatment of AG1478 (100 nM) when the cells were treated with the conditioned-medium (CM, 24 hours) of LX2 cell line known as the activated hepatic stellate cells together with DMSO or AG1478, the EFGR kinase inhibitor.

As a result, as EGFR signaling was inhibited by AG1478, TM4SF5 expression was also reduced, suggesting that EGFR signal transduction system played a crucial role in TM4SF5 expression (FIG. 12).

(6) Even though TM4SF5 expression was inhibited by the suppression of EGFR activation by AG1478, it did not affect TGFβ signaling Smad2 activation. Therefore, it is presumed that TGFβ mediated receptor-regulated Smad (R-Smad) activation induces EGFR signal transduction system activation and then the activated EGFR signal transduction system induces TM4SF5 expression stepwise. Next, TGFβ signal transduction system was activated by using adenoviruses of Smad2 and Smad3, known as R-Samd, and Smad4, known as common-mediator Smad (co-Smad) to investigate the effect on EGFR signal transduction system and TM4SF5 expression.

To activate TGFβ signal transduction system, Chang cells were infected with Samd2, Smad3, and Smad4 adenoviruses (Lee M S et al., Mol Cell Biol. 2005 August; 25(16):6921-36) for 24 hours. After serum starvation, the cells were treated with TGFβ for 24 hours, from which cell extract was obtained. LacZ adenovirus (Lee M S et al., Mol Cell Biol. 2005 August; 25(16):6921-36) was used as the control virus.

The protein in the cell extract was quantified, followed by Western blotting with antibodies against phospho-$Y^{1173}$EGFR, EGFR, FLAG (Cell Signaling Technology, Danvers, Mass.), α-tubulin, and TM4SF5.

Figure 13:
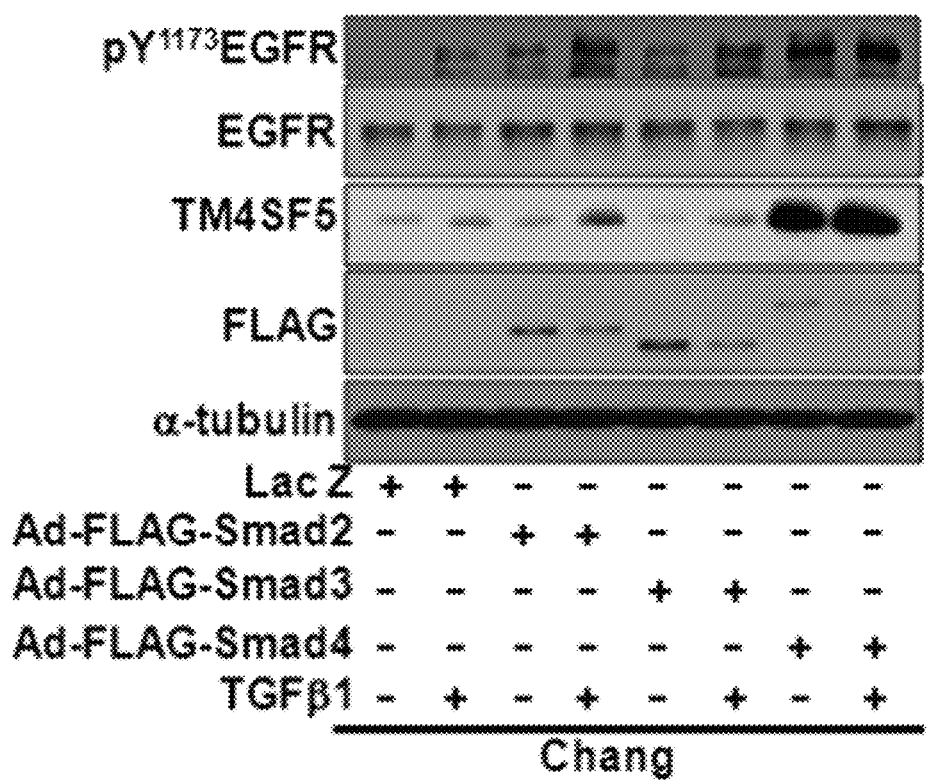
FIG. 13 is a set of photographs illustrating the results of Western blotting performed to confirm TM4SF5 expression in Chang cells in which Smad2, Smad3, or Smad 4 was over-expressed by being infected with adenovirus for 24 hours over the treatment of TGFβ.

As a result, it was confirmed that TM4SF5 expression was increased in the group treated with Smad2 adenovirus TGFβ dependently. In the group treated with Smad3 adenovirus, TM4SF5 level was not much different from that of the control. The above results suggested that Smad2 was the major R-Smad involved in TGFβ mediated TM4SF5 expression. In the group treated with Smad4 adenovirus, TM4SF5 expression was increased by the over-expression of Smad4. At this time, TM4SF5 expression was more induced by TGFβ, in which EFGR signal transduction system activation was involved (FIG. 13).

Figure 14:
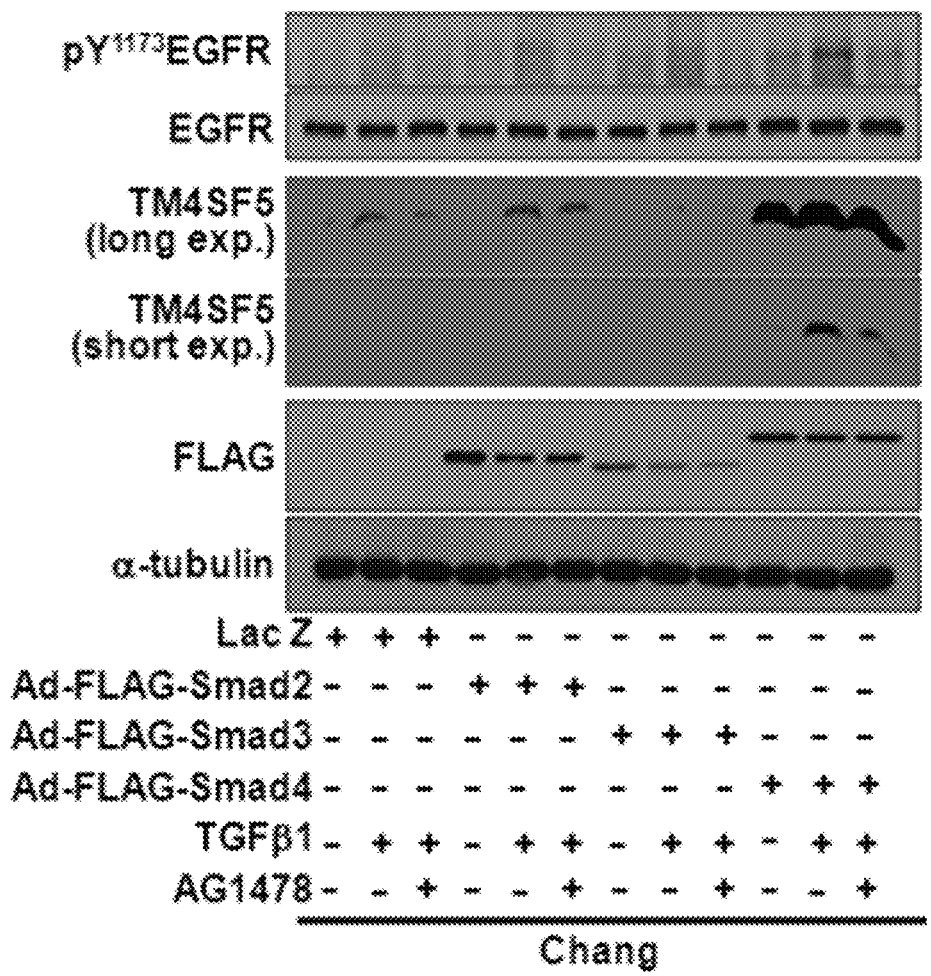
FIG. 14 is a set of photographs illustrating the results of Western blotting performed to confirm TM4SF5 expression level over the treatment of TGFβ in Chang cells in which Samd2, Samd3, or Smad4 was over-expressed by being infected with adenovirus for 24 hours after treated or not treated with AG1478.

In addition, Chang cells were infected with Smad2, Smad3, and Smad4 adenoviruses for 24 hours, followed by serum starvation for 24 hours. After serum starvation, the cells were treated with AG1478 1 hour before the treatment of TGFβ in order to inhibit EGFR signaling. After the treatment of TGFβ, the cells were further cultured for 24 more hours. Then, the protein in the cell extract was quantified, followed by Western blotting. As a result, it was confirmed that TGFβ mediated TM4SF5 expression was reduced by AG1478 in the group treated with Smad2 and Smad4 adenoviruses. Therefore it was suggested that EFGR signal transduction system activation played an important role in inducing TGFβ mediated TM4SF5 expression (FIG. 14).

(7) Following experiment was performed to investigate whether or not EGFR activation that has been confirmed to be involved in TGFβ mediated TM4SF5 expression would be involved in recycling or trafficking of internalized EGFR.

Particularly, Chang cells were infected with Smad4 adenovirus for 24 hours. After serum starvation, the cells were treated with TGFβ, followed by culture for 24 hours at 4° C. to inhibit recycling or trafficking of internalized EGFR.

Figure 15:
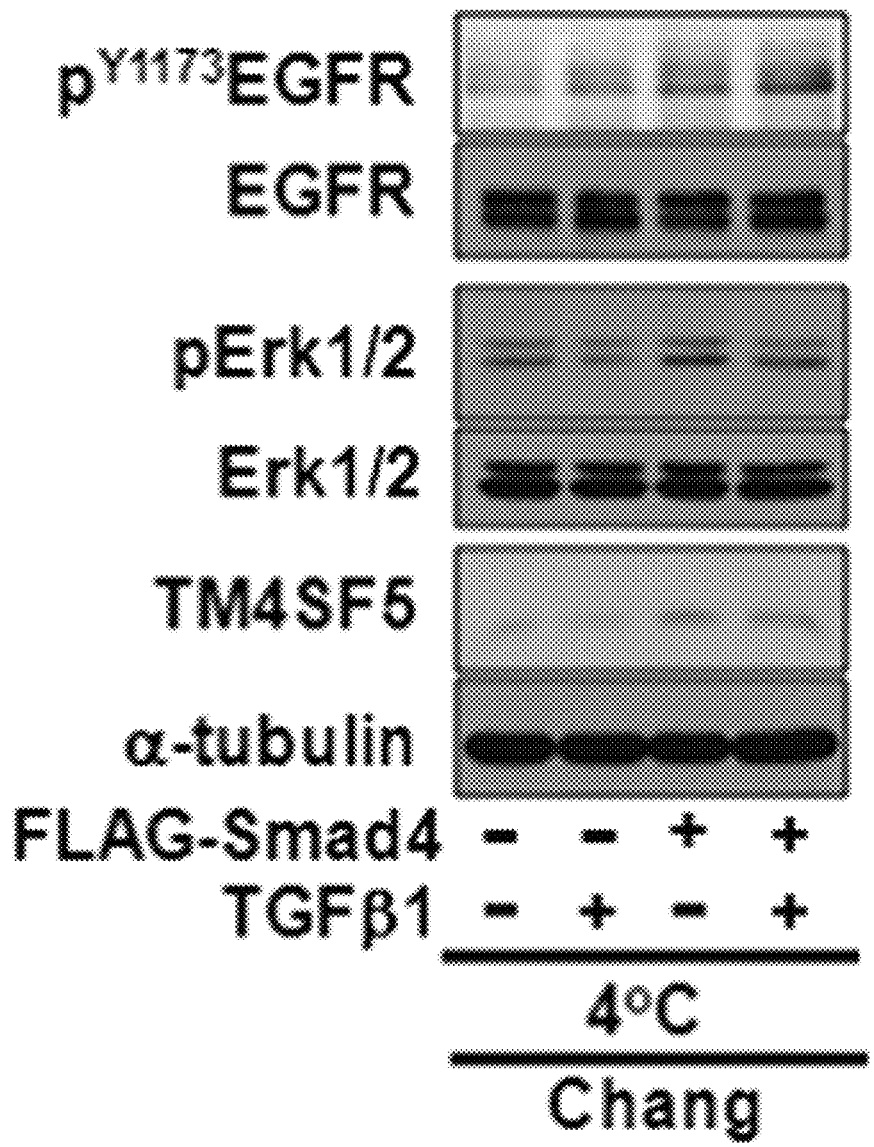
FIG. 15 is a set of photographs illustrating the results of Western blotting performed to confirm TM4SF5 expression and phospho-$Y^{1173}$ EGFR levels in Chang cells according to the treatment of TGFβ at 4° C.

As a result, it was confirmed that EGFR signaling activation and TM4SF5 expression were induced a little bit without EGFR up-regulation in the group treated with Smad4 adenovirus after the cells were cultured at 4° C. in the presence of TGFβ (FIG. 15). Therefore, it was suggested that internalized EGFR recycling was not involved in EGFR activation in relation to TGFβ mediated TM4SF5 expression.

(8) To investigate whether or not the increase of TM4SF5 expression induced by Smad4 adenovirus would be attributed to Smad4 mediated EGFR protein synthesis, cycloheximide (Sigma), the protein synthesis inhibitor, was used for the following experiment.

Particularly, Chang cells were infected with Smad4 adenovirus for 24 hours. After serum starvation, the cells were treated with cycloheximide (100 µg/ml) to inhibit protein synthesis. 24 hours later, the protein in the cell extract was quantified, followed by Western blotting.

Figure 16:
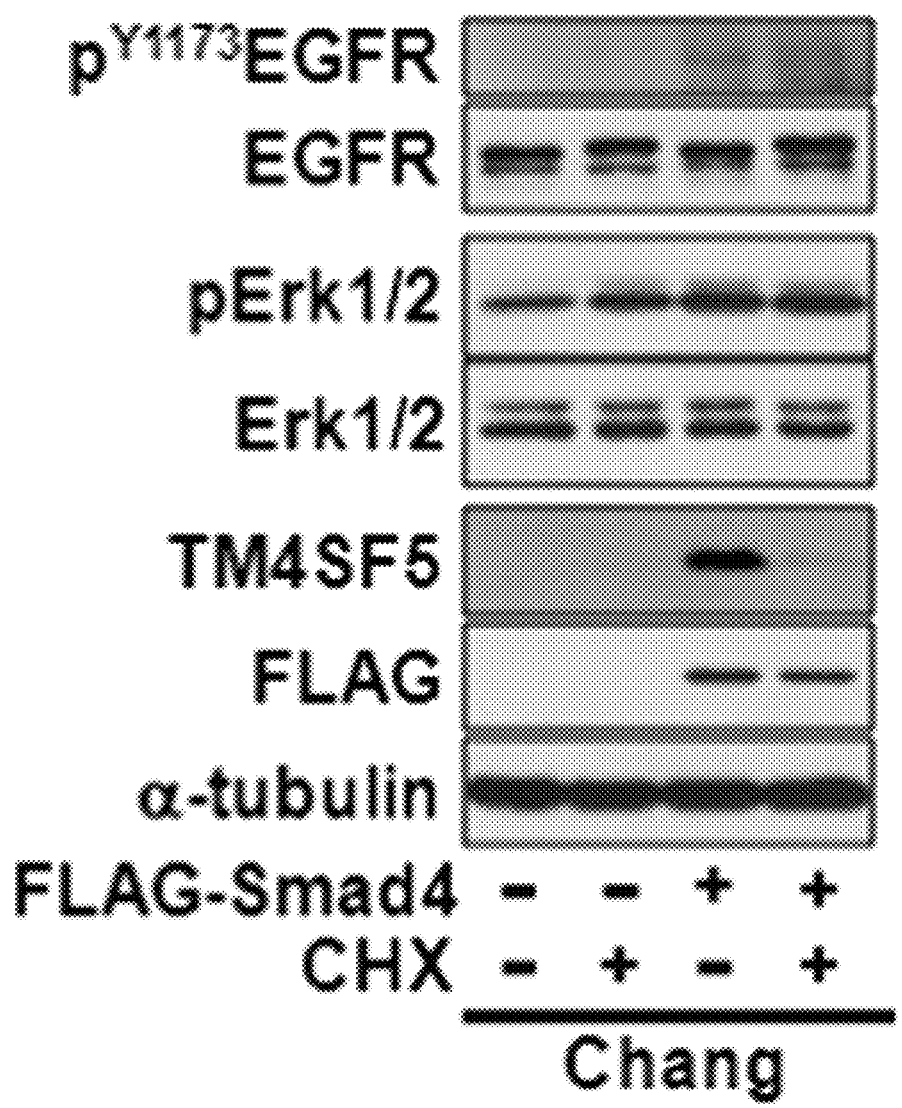
FIG. 16 is a set of photographs illustrating the results of Western blotting performed to confirm TM4SF5 expression level in Chang cells in which Smad 4 was over-expressed by being infected with adenovirus for 24 hours after treated or not treated with cycloheximide.

As a result, EGFR expression in the group treated with Smad4 adenovirus was similar to that of the control group treated with control virus. However, EGFR signaling activation was increased by Smad4 expression. Therefore, it was confirmed that EGFR synthesis was not involved in EGFR signal transduction system activation induced by Smad4 over-expression (FIG. 16).

(9) AML12 cells and Chang cells were collected from cell culture vessels by using 0.05% trypsin-EDTA, which were transferred in the medium supplemented with 1% BSA, followed by rolling for 1 hour (60 rpm). The cells were treated with TGFβ (5 ng/ml) 15 minutes before the cells were reseeded in the cell culture vessel pre-coated with fibronectin or in the condition of suspension to prevent cell adhesion. Those cells left in the suspension were unattached, while those cells reseeded in the vessel coated with fibronectin were reattached. 12 hours later, the cells were harvested, followed by Western blotting to investigate TM4SF5 expression.

Figure 17:
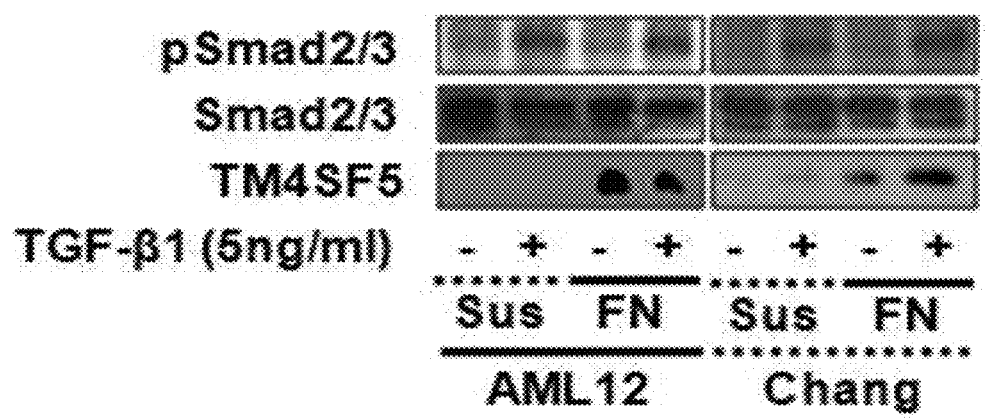
FIG. 17 is a set of photographs illustrating the results of Western blotting performed to confirm TM4SF5 expression level over the treatment of TGFβ in AML12 cells and in Chang cells either in suspension status or re-seeded status in fibronectin-coated vessel.

As a result, TM4SF5 expression was confirmed in the cells in the vessel coated with fibronectin, suggesting that TGFβ mediated TM4SF5 expression was dependent on cell adhesion signal (FIG. 17).

Example 4

Confirmation of TM4SF5 Expression Change Over the Inhibition of TGFβ Signal Transduction System by Inhibitory-Smad In the above examples, it was confirmed that TM4SF5 expression was induced by TGFβ mediated EGFR signal transduction system activation. The following experiment was performed to inhibit TGFβ signal transduction system by using Smad7 adenovirus known as inhibitory-Smad.

To inhibit TGFβ signal transduction system, Chang cells and AML12 cells were infected with Smad7 adenovirus (Lee M S et al., Mol Cell Biol. 2005 August; 25(16):6921-36) for 24 hours. After serum starvation, the cells were treated with TGFβ. 24 hours later, cell extract was obtained. LacZ adenovirus (Lee M S et al., Mol Cell Biol. 2005 August; 25(16): 6921-36) was used as the control virus.

The protein in the cell extract was quantified, followed by Western blotting using antibodies against phospho-EGFR$^{Y1045}$, phospho-EGFR$^{1992}$, phospho-EGFR$^{Y1173}$, EGFR, phospho-Erk, Erk, phospho-Smad2, phospho-Smad3, phospho-Smad2/3, α-SMA, α-tubulin, and TM4SF5.

Figure 18:
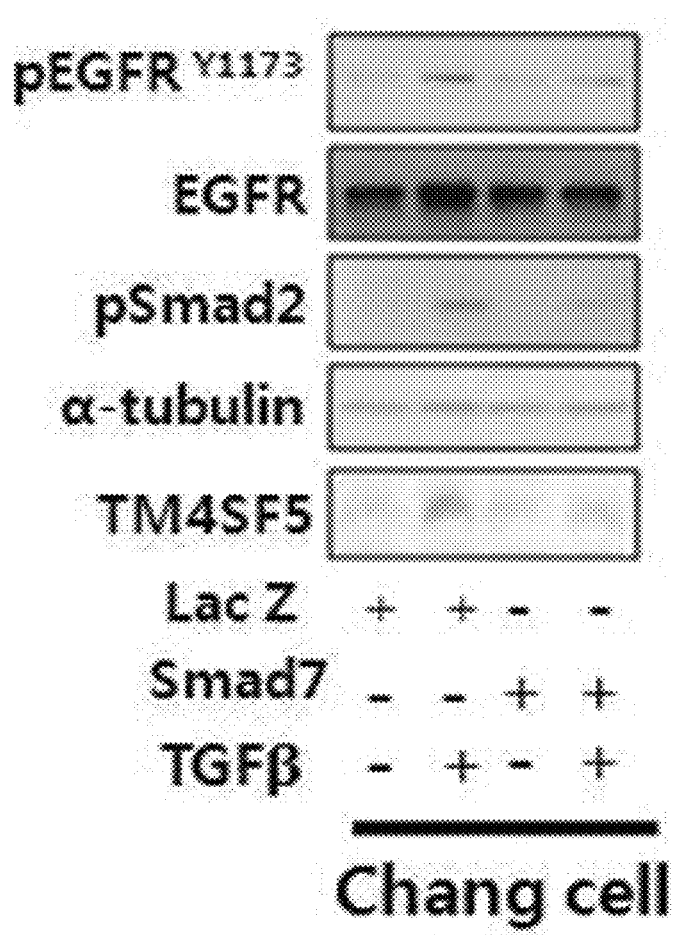
FIG. 18 is a set of photographs illustrating the results of Western blotting performed to confirm TM4SF5 expression level according to the treatment of TGFβ after inducing the expression in Chang cells by infecting the cells with the control virus (LacZ) or Smad 7-adenovirus for 24 hours.

As a result, as shown in FIG. 18, TM4SF5 expression was reduced in Chang cells infected with Smad7 adenovirus. Smad2 phosphorylation and EGFR phosphorylation were increased by the treatment of TGFβ, but reduced by Smad7.

Figure 19:
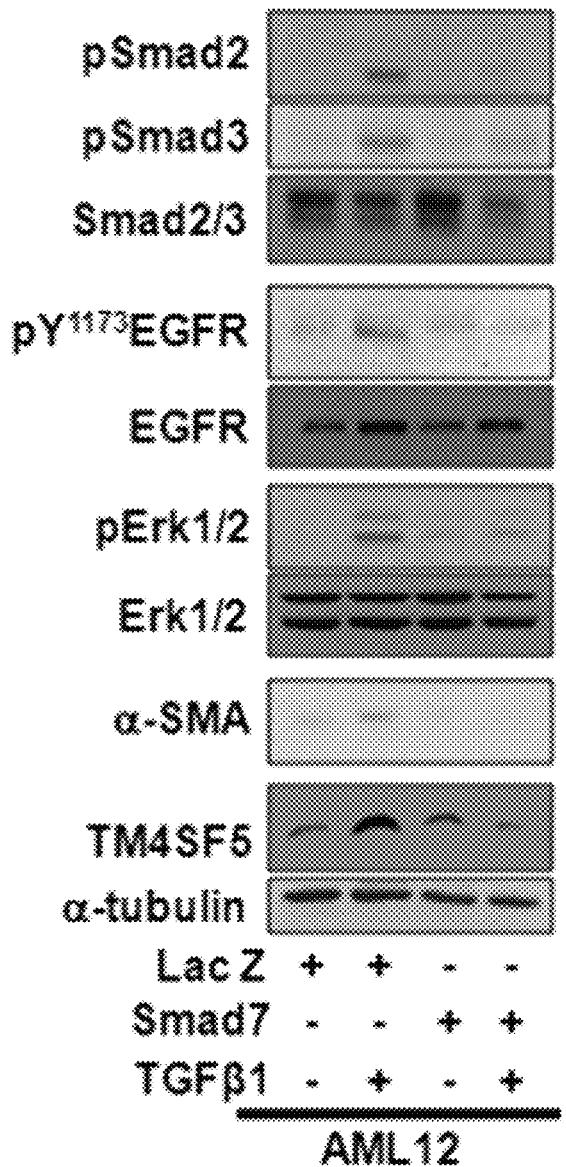
FIG. 19 is a set of photographs illustrating the results of Western blotting performed to confirm the expression levels of TM4SF5 and α-SMA, and the phosphorylation levels of phospho-$Y^{1173}$ EGFR and Smad2/3 according to the treatment of TGFβ after inducing the expression in AML12 cells by infecting the cells with the control virus (LacZ) or Smad 7-adenovirus for 24 hours.

As shown in FIG. 19, TM4SF5 expression was induced in AML12 cells by TGFβ and at this time EFGR phosphorylation, Erk phosphorylation, and Smad2/3 phosphorylation were accompanied. In addition, the expression of α-SMA, the mesenchymal cell marker, was increased, confirming EMT. However, once Smad7 was treated thereto, Smad2/3 phosphorylation, EFGR phosphorylation, and Erk phosphorylation were all reduced along with the decrease of TM4SF5 expression. The expression of α-SMA was also decreased. Therefore, it was confirmed that TGFβ mediated TM4SF5 expression was inhibited therein and EFGR signal transduction system was inactivated (FIG. 18 and FIG. 19). From the above results, it was also confirmed that TM4SF5 expression was induced by TGFβ mediated Smad protein activation and EFGR signal transduction system activation.

Example 5

Confirmation of TM4SF5 Expression in the Progress of Liver Disease Such as Hepatic Fibrosis and Liver Cirrhosis To investigate TM4SF5 expression in relation to chronic hepatic injury, animal test using mice was performed.

Balb/c female mice (4 weeks old, 20 g) were used. The animals were fed with sterilized water and feeds. For the biological day/night cycle, the indoor light was turned on for 12 hours and off for 12 hours. The mice were divided into two groups, which were each treated with $CCl_4$ and ethanol. Each group was composed of 16 mice. The $CCl_4$ group mice were treated with 40% $CCl_4$ diluted in olive oil by intraperitoneal administration (1 mg/kg, 3 times/week). The mice were sacrificed by using ether [4 mice (one mouse from the control group, 3 mice from the experimental group) per week for 4 weeks].

The ethanol group mice were orally administered with ethanol (20% ethanol for the first week, 30% ethanol for the second week, 40% ethanol for the third week, and 50% ethanol for the fourth week). The mice were sacrificed by using ether [4 mice (one mouse from the control group, 3 mice from the experimental group) per week for 4 weeks].

The liver tissues obtained from the sacrificed mice were incised for immunohistochemical test. Some of the tissues were fixed in formaldehyde, followed by preparing paraffin samples. The paraffin sections in the thickness of 4-5 µm were fixed on slide, followed by H&E (hematoxylin and eosin) staining and immunohistochemical test. Deparaffination using xylene and dehydration (100%>90%>80%>70% ethanol) were performed. Then, the slide was loaded in 10 mM citrate buffer (pH 6.0), which was boiled for 10 minutes for antigen retrieval. The slide was cooled down at room temperature, which was soaked in 3% hydrogen peroxide in methanol for 10 minutes, followed by quenching of endogenous peroxidase. The slide was blocked with 6% normal horse serum for 30 minutes, followed by reaction with the antibody against TM4SF5 (Sin-Ae Lee et al., J. Clin. Invest., 2008 April; 118(4):1354-66) at 4° C. for overnight. The slide was reacted with biotinylated secondary antibody (the secondary antibody against rabbit antibody, Calbiochem, San Diego, Calif.) in ABC solution (Vector Lab, USA) at room temperature for 1 hour. The reaction was investigated by using 3,3-diaminobenzidine chromogen & substrate buffer (DAB). Counter staining was performed with hematoxylin, followed by observation under microscope at 100× and 400× after mounting with permanent aqueous medium.

To confirm collagen synthesis, Masson's trichrome staining was performed with the kit purchased from Sigma Aldrich. First, the paraffin section fixed on the slide was reacted with Bouin's solution, followed by reaction with Weigert's Iron hematoxylin solution to dye the nucleus. Next, cytoplasm was stained with Biebrich Scarlet-acid Fucshin. Then, collagen I was stained with aniline blue solution. Lastly, the slide was mounted with permanent aqueous medium, followed by observation under microscope at 100× and 400×.

Figure 20:
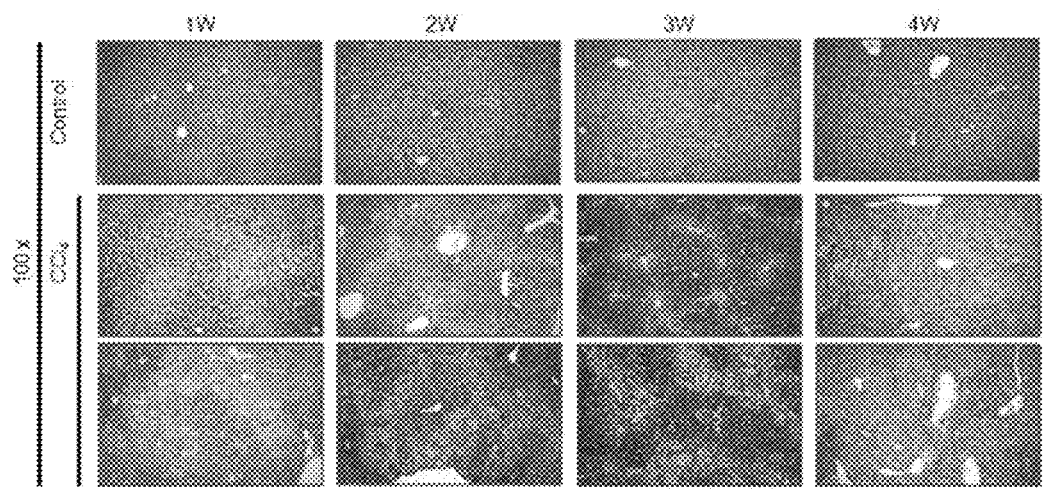
FIG. 20 is a set of photographs illustrating the results of H&E staining performed with liver tissues obtained from both normal mice and $CCl_4$ treated mice, confirming hepatic injury.

As a result, as shown in FIG. 20, unlike normal liver tissues in which nucleus and cytoplasm were evenly stained by H&E staining, the liver tissues obtained from the $CCl_4$ treated mice showed clogged nuclei and destroyed cytoplasm, indicating hepatic injury (FIG. 20).

Figure 21:
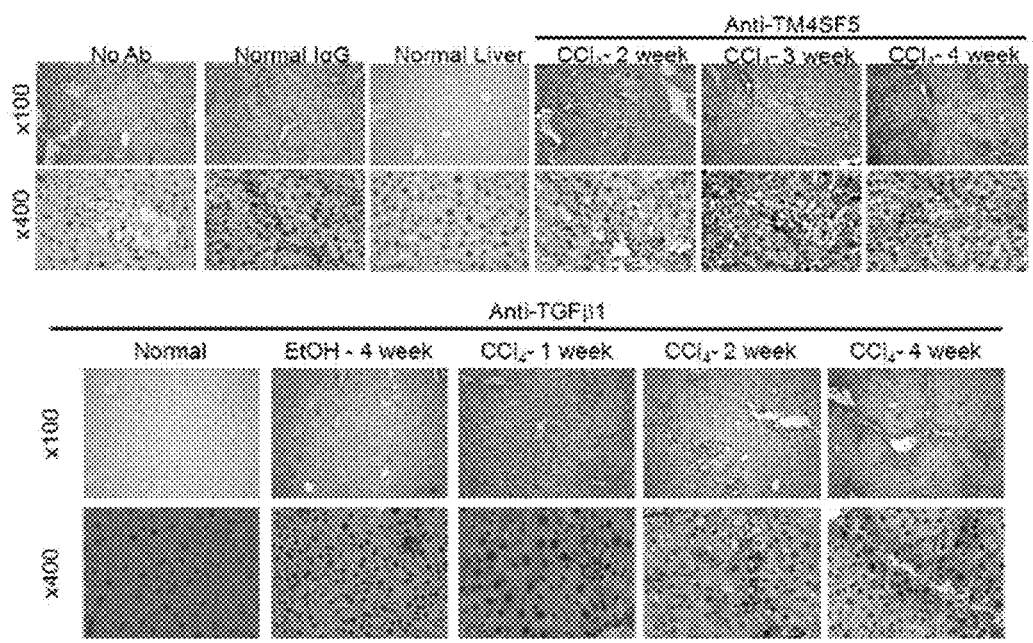
FIG. 21 is a set of photographs illustrating the results of immunohistochemical staining performed to confirm TGFβ or TM4SF5 expression in liver tissues of normal mice and $CCl_4$ treated mice.

As shown in FIG. 21 and FIG. 22, it was confirmed by immunohistochemical staining by using the antibodies described in Example 3 that TGFβ secretion, TM4SF5 expression, and α-SMA (antibodies were purchased from Sigma-Aldrich) expression were all induced along with the activation of pERK and $pEGFR^{Y1173}$ over hepatic injury. The above expressions were correlated in the damaged area of the liver.

Figure 23:
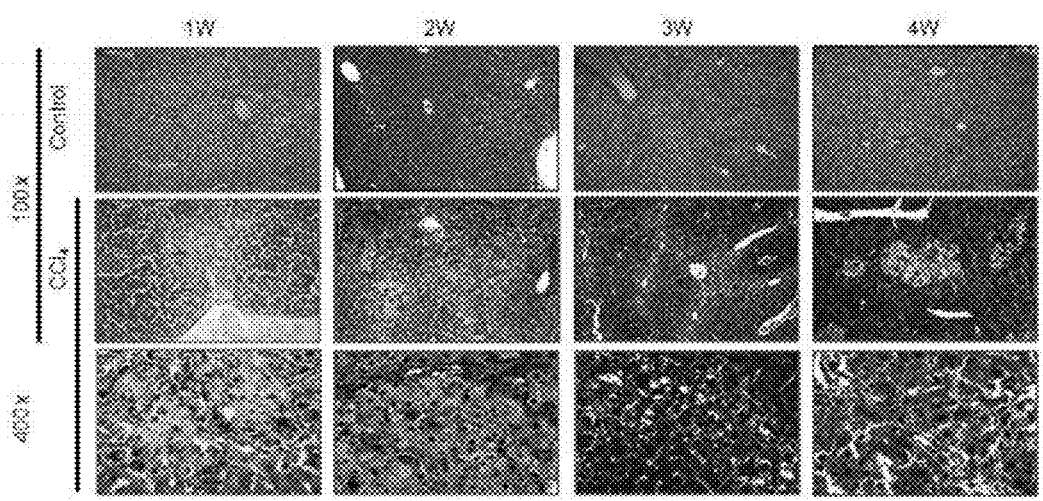
FIG. 23 is a set of photographs illustrating the results of collagen staining performed to confirm the accumulation of collagen type I and fibrosis in liver tissues of normal mice and $CCl_4$ treated mice.

As shown in FIG. 23, it was confirmed by collagen staining experiment that collagen synthesis in the damaged liver area was increased with inducing fibrosis. The location where collagen I was expressed was consistent with the locations where TGFβ, TM4SF5, and α-SMA were expressed, suggesting that TM4SF5 was involved in the progress of liver disease.

Figure 24:
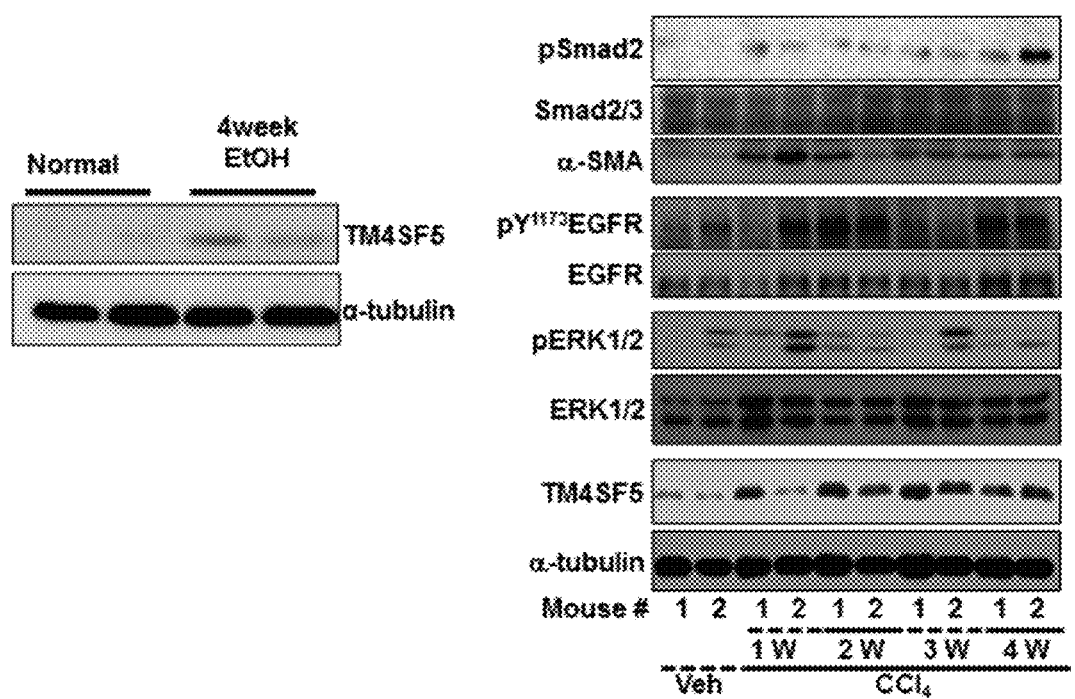
FIG. 24 is a set of photographs illustrating the results of Western blotting performed to confirm the levels of TM4SF5 expression, phospho-$Y^{1173}$ EGFR and Smad2 phosphorylation in liver tissues of normal mice, alcohol treated mice and $CCl_4$ treated mice.

Some tissues extracted from the liver of the mouse having hepatic injury were frozen in liquid nitrogen until use. The tissues were pulverized by using homogenizer and lysed by using lysis buffer. The lysate was quantified and the same amount of protein was used for each experiment. The protein was isolated by using 8~12% SDS gel, followed by immunoblotting using antibodies against pSmad2, TM4SF5, and α-tubulin. As a result, as shown in FIG. 24, TM4SF5 expression was increased in the $CCl_4$ treated group, unlike the control, and so were the activations of Smad, the TGFβ signal transduction system, and EGFR signal transduction system.

Example 6

Investigation of the Action of TM4SF5 Antagonist in Liver Disease

Based on the fact that TSAHC [4'-(p-toluenesulfonylamino)-4-hydroxychalcone] could be functioning as TM4SF5 antagonist (ex: EMT is specifically inhibited), the present inventors investigated whether or not TM4SF5 could be inhibited by using the antagonist TSAHC in the process of hepatic fibrosis and liver cirrhosis.

First, normal hepatocytes were treated with TGFβ to induce TM4SF5 expression and EMT, during which TSAHC was treated. As described hereinbefore, the normal hepatocytes were washed with serum-free DMEM, followed by serum starvation for 4 hours. Then, the cells treated with TGFβ to induce TM4SF5 expression. 6 hours later, the cells were treated with TSAHC at the concentration of 5 μM or 10 μM, followed by culture for 18 hours. The expression of α-SMA protein was investigated.

Figure 25:
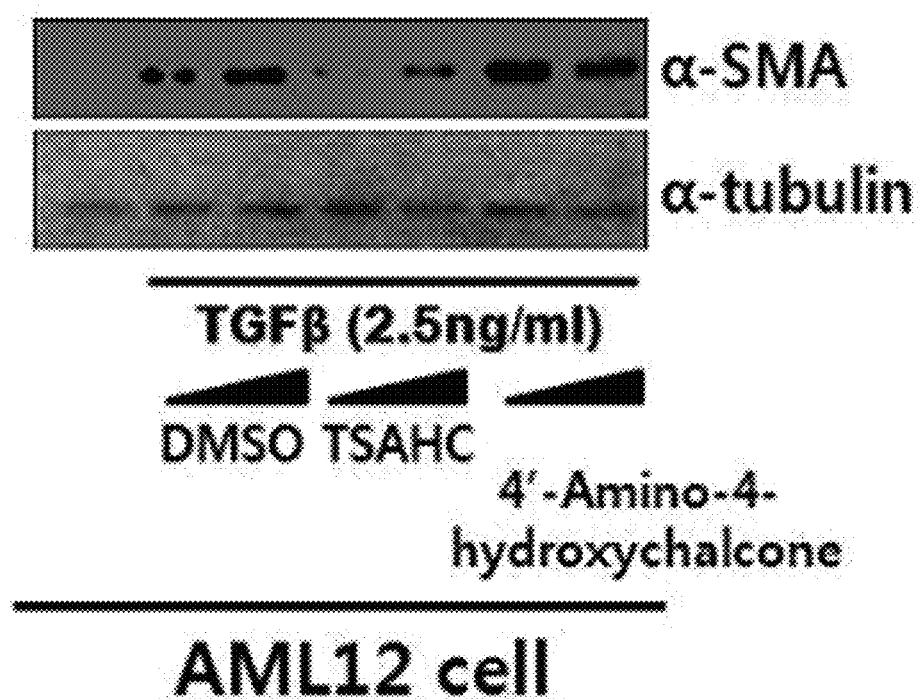
FIG. 25 is a set of photographs illustrating the results of Western blotting performed to confirm the level of α-SMA expression induced by TGFβ in AML12 cells treated with TSAHC and 4'-amino-5-hydroxychalcone.

As a result, as shown in FIG. 25, it was confirmed that TGFβ mediated α-SMA expression was significantly reduced by the treatment of TSAHC. For the comparison, the cells were treated with the control compound that had similar structure to TSAHC but had substituted R residue (4'-amino-4-hydroxychalcone) at the same concentration as the above (5 μM or 10 μM). As a result, the control compound did not affect the expressions of TM4SF5 and α-SMA alpha (FIG. 25).

Figure 26:
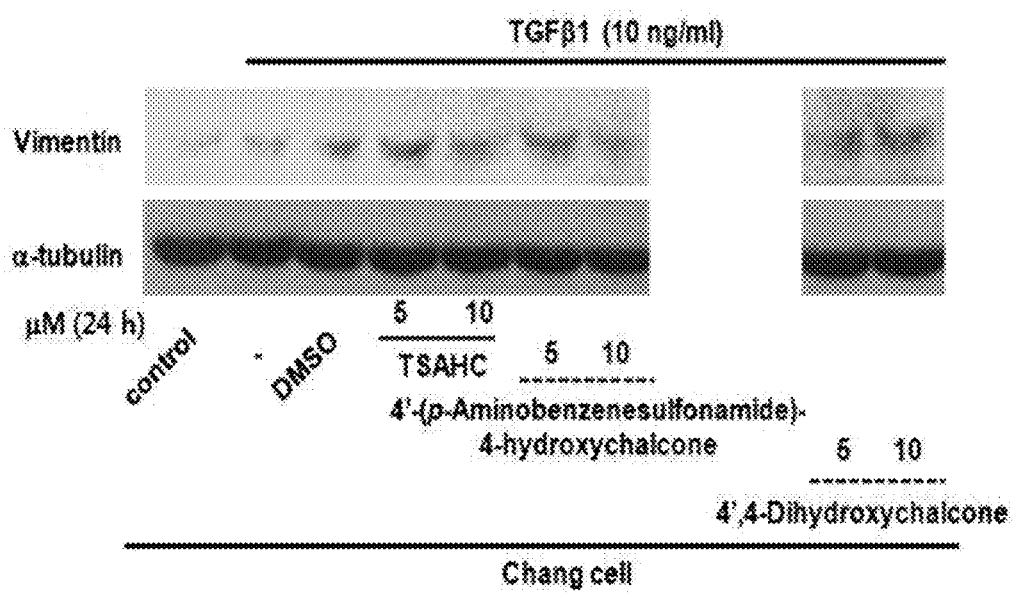
FIG. 26 is a set of photographs illustrating the results of Western blotting performed to confirm the level of vimentin expression mediated by TGFβ in Chang cells treated with TSAHC, 4'-(p-aminobenzenesulfoneamide)-4-hydroxychalcone, and 4,4-dihydroxychalcone.
Figure 27:
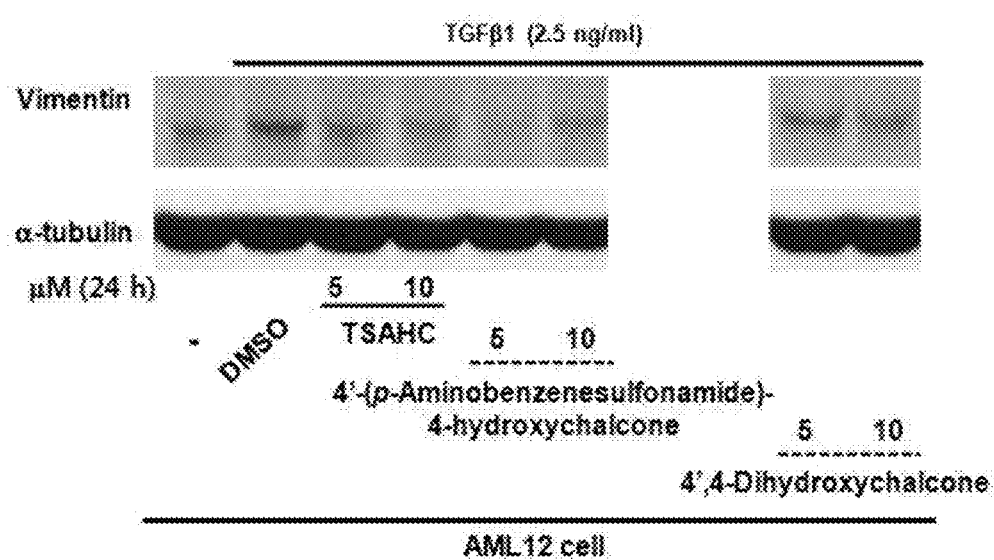
FIG. 27 is a set of photographs illustrating the results of Western blotting performed to confirm the level of vimentin expression mediated by TGFβ in AML12 cells treated with TSAHC, 4'-(p-aminobenzenesulfoneamide)-4-hydroxychalcone, and 4,4-dihydroxychalcone.

In addition, 4'-(p-aminobenzenesulfonamide)-4-hydroxychalcone (ASAHC), the water-soluble inducer, was treated to AML12 and Chang cells at the concentration of 5 μM or 10 μM. Like the case of treating TSAHC, the mesenchymal cell marker vimentin was down-regulated, compared with the case of treating TGFβ1, suggesting that ASAHC could also inhibit the up-regulation of vimentin induced by TGFβ1 mediated TM4SF5 expression and EMT (FIG. 26 and FIG. 27). However, when the other control compound 4'4-dihydroxychalcone was treated to those cells, TGFβ1 mediated vimentin expression was not much changed, suggesting that this compound was not involved in TM4SF5 expression, unlike TSAHC and ASAHC (FIG. 26 and FIG. 27).

From the above results, it was confirmed that TGFβ induced TM4SF5 expression and increased α-SMA expression thereafter, indicating that epithelial cells were transformed to mesenchymal cells. In the meantime, α-SMA expression was inhibited by the treatment of TSAHC. At the same time, EFGR/Erk phosphorylation was also reduced. In conclusion, TGFβ induced TM4SF5 expression, which induced EMT thereby, and on the contrary TSAHC suppressed TGFβ mediated α-SMA expression.

Therefore, TSAHC acting as an antagonist against TM4SF5 seemed to inhibit the expressions and phosphorylations of TM4SF5 mediated signal transduction related proteins which play an important role in overall hepatic injury including liver cancer, hepatic fibrosis, and liver cirrhosis, suggesting that TSAHC could be a candidate for the inhibition of liver disease.

Example 7

Inhibition of Hepatic Injury and Hepatic Fibrosis by TSAHC, the Material Suppressing TM4SF5 Expression and the Expressions and Phosphorylations of TM4SF5 Related Signaling Proteins The following experiment was performed with mice to investigate whether or not the material suppressing TM4SF5 expression and the expressions and phosphorylations of TM4SF5 related signaling proteins could reduce or prevent hepatic injury.

Balb/c mice (5 weeks old, n=5) were used. The mice were fed with sterilized water and feeds. For the biological day/night cycle, the indoor light was turned on for 12 hours and off for 12 hours. The mice were treated with $CCl_4$ or ethanol for 2 weeks. The $CCl_4$ group mice were treated with 40% $CCl_4$ diluted in olive oil by intraperitoneal administration (1 mg/kg, 3 times/week). The $CCl_4$-ContComp group mice were treated with 4'-Amino-4-hydroxychalcone, the control compound (ContComp), every other day and every next day of $CCl_4$ treatment by IP (intraperitoneal injection) or oral administration (50 mg/kG, 40% DMSO, 3 times/week). The $CCl_4$-TSAHC group mice were treated with TSAHC every other day and every next day of $CCl_4$ treatment by IP (intraperitoneal injection) or oral administration (50 mg/kG, 40% DMSO, 3 times/week).

Two weeks later, the mice were sacrificed by using ether. The liver was extracted from the sacrificed animal of each group. Paraffin samples were prepared by the same manner as described in Example 5. The paraffin sections in the thickness of 4-5 μm were fixed on slide, followed by H&E (hematoxylin and eosin) staining for the confirmation of hepatic injury, Masson's Trichrome duator staining for collagen type I staining, and immunihistochemistry with the antibody (1:1500) against α-SMA (smooth muscle actin, Sigma).

Figure 28:
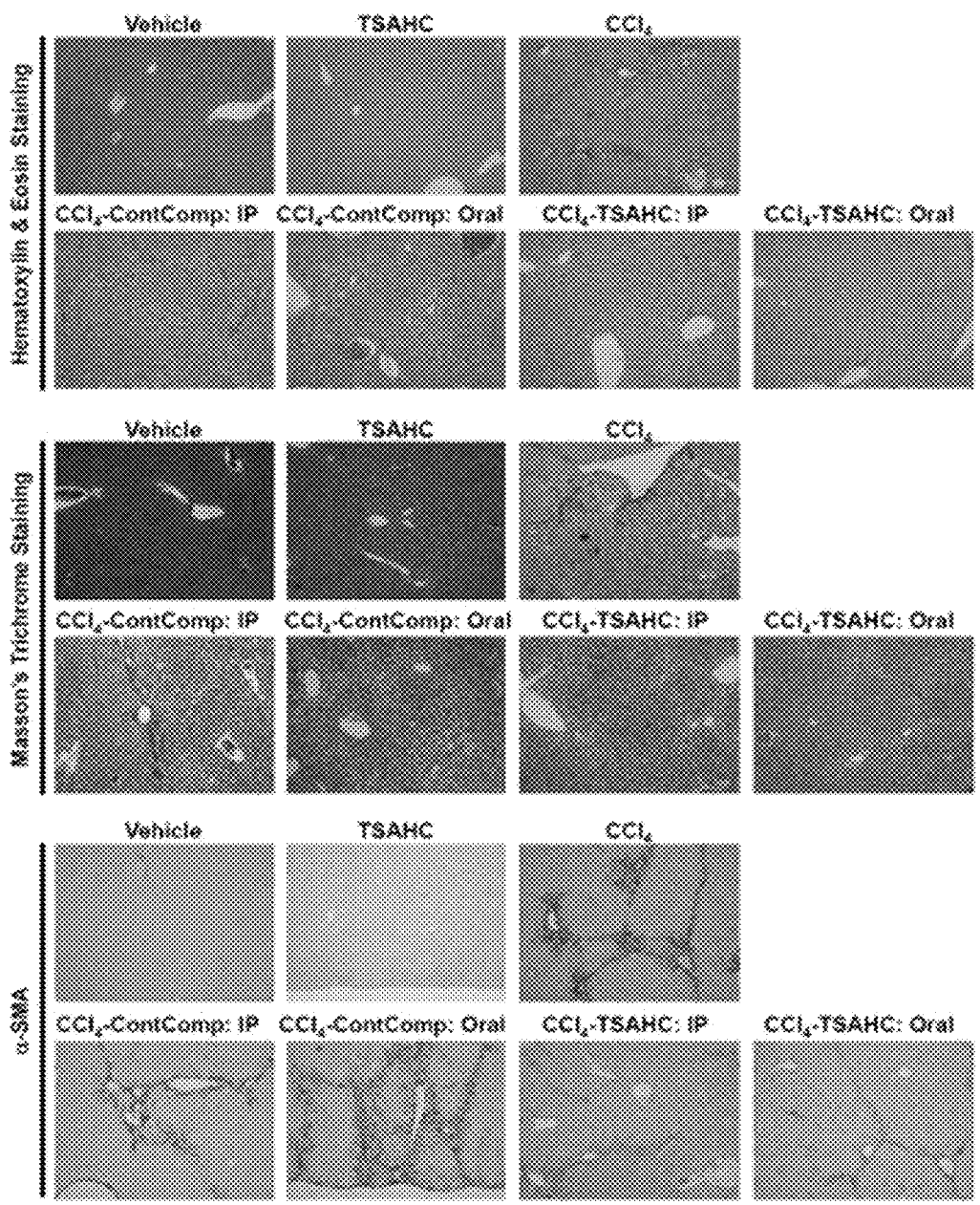
FIG. 28 is a set of photographs illustrating the results of immunohistochemical staining performed to confirm the levels of hepatic injury (H&E staining), collagen type I expression (Masson's Trichrome duator staining), and α-SMA expression in liver tissues obtained from ethanol treated group (Vehicle), TSAHC treated group (TSAHC), $CCl_4$ treated group, $CCl_4$-ContComp group (treated with $CCl_4$ together with 4'-amino-4-hydroxychalcone, the Control compound), and $CCl_4$-TSAHC group (treated with $CCl_4$ together with TSAHC).

As a result, as shown in FIG. 28, nucleus and cytoplasm of the group treated with ethanol (Vehicle) or TSAHC only (TSAHC) were evenly stained by H&E staining, which was the sign of normal liver. In the meantime, in the group treated with $CCl_4$, hepatic injury was observed. In the group treated with $CCl_4$ together with TSAHC, the TM4SF5 inhibitor, hepatic injury was reduced by both oral administration and IP (intraperitoneal injection) of TSAHC. However, in the CCl$_4$-ContComp group treated with CCl$_4$ and 4'-Amino-4-hydroxychalcone, the control compound, CCl$_4$ dependency was not observed.

From the result of Masson's Trichrome staining, it was confirmed that collagen type I expression was reduced in the group treated with CCl$_4$ together with TSAHC(CCl$_4$-TSAHC) via oral administration or IP (intraperitoneal injection), while such reduction was not detected in the CCl$_4$-ContComp group. From the result of α-SMA immunohistochemical staining, it was also confirmed that that α-SMA expression was reduced by the treatment of TSAHC. The decrease of α-SMA expression indicated the reduction of EMT (epithelial-mesenchymal transition) in hepatocytes necessary for hepatic fibrosis.

Additionally, two mice were randomly selected from each group, from which liver tissue extract was prepared. The protein in the extract was quantified, followed by Western blotting with antibodies against phospho-Y$^{1173}$EGFR (Santa Cruz Biotechnology, Santa Cruz, Calif.), phospho-Y$^{1068}$EGFR (Santa Cruz Biotechnology, Santa Cruz, Calif.), EGFR (Santa Cruz Biotechnology, Santa Cruz, Calif.), phospho-Erk (Cell Signaling Technology, Danvers, Mass.), Erk (Cell Signaling Technology, Danvers, Mass., USA), phospho-Smad3 (Cell Signaling Technology, Danvers, Mass.), TM4SF5 (antibody of Example 1), α-SMA (smooth muscle actin, Sigma), phospho-S$^{10}$-p27 (Santa Cruz Biotechnology, Santa Cruz, Calif., USA), p27 (BD Transduct. Lab. San Jose Calif., USA), and α-tubulin (Sigma-Aldrich).

Figure 29:
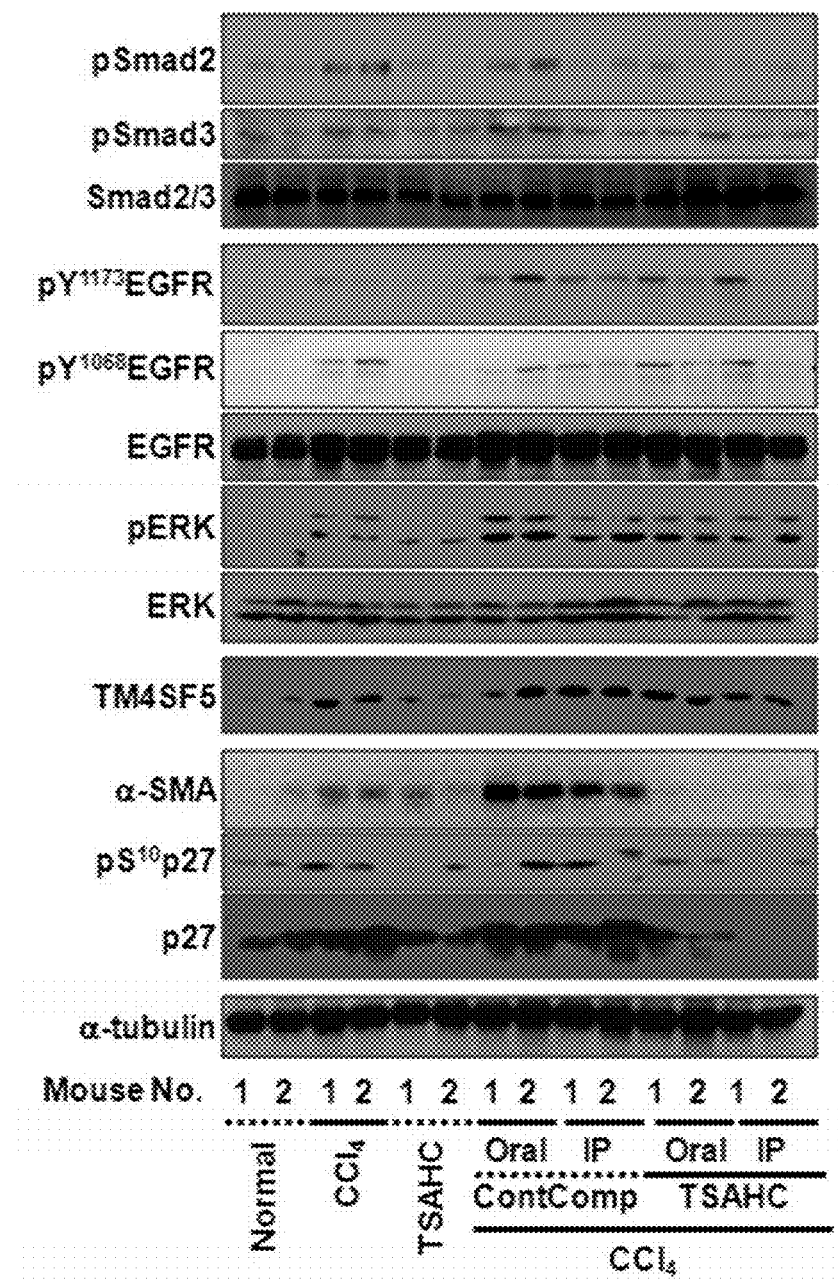
FIG. 29 is a set of photographs illustrating the results of Western blotting performed to confirm the levels of Smad3 phosphorylation, EGFR/Erk phosphorylation and activation, TM4SF5 expression and α-SMA expression in liver tissues obtained from ethanol treated group (Vehicle), TSAHC treated group (TSAHC), $CCl_4$ treated group, $CCl_4$-ContComp group (treated with $CCl_4$ together with 4'-amino-4-hydroxychalcone, the Control compound), and $CCl_4$-TSAHC group (treated with $CCl_4$ together with TSAHC).

As shown in FIG. 29, TM4SF5 signal transduction process (phosphorylation of Smad3, the down-stream factor of TGFβ1, phosphorylation and activation of EFGR/Erk) was not affected by TSAHC and control compound, either. However, α-SMA expression induction, one of the functions of expressed TM4SF5, EMT, p27 expression, and Ser10 phosphorylation induction were all inhibited in the liver tissue of the group treated with TSAHC. In the meantime, in the group treated with the control compound, 4'-Amino-4-hydroxychalcone, the said inductions mediated by CCl$_4$-dependent TM4SF5 expression were not inhibited. That is, TM4SF5 activity was suppressed by TSAHC.

The above results indicate that the material inhibiting TM4SF5 protein expression or activity, precisely the material suppressing TM4SF5 expression and the expressions and phosphorylations of TM4SF5 related signaling proteins can be effectively used for the prevention and treatment of liver disease by inhibiting hepatic injury and hepatic fibrosis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for screening a material for treating hepatic fibrosis comprising the following steps:
   1) contacting hepatocytes expressing TM4SF5 (Transmembrane 4 L six family member 5 or Four-Transmembrane L6 Superfamily member 5) protein a with candidate material;
   2) measuring the expression of TM4SF5 protein by using an antibody raised against amino acids 77-197 of SEQ ID NO:2; and
   3) selecting a candidate material that inhibits the expression of TM4SF5 protein, by comparing the expression to a control group not treated with the candidate material of step 1).

2. The method for screening a material for treating hepatic fibrosis according to claim 1, wherein the TM4SF5 protein is the polypeptide of SEQ. ID. NO: 2.

3. A method for screening a material for treating hepatic fibrosis comprising the following steps:
   1) generating an animal model for liver disease or hepatic injury by injecting or administering CCl4, followed by administering a candidate material for treating hepatic fibrosis to the animal model;
   2) measuring expression of TM4SF5 protein by using an antibody raised against amino acids 77-197 of SEQ ID NO:2; and
   3) selecting a candidate material for treating hepatic fibrosis that is confirmed to change the expression levels of one or more proteins selected from the group consisting of α-SMA, vimentin, cytoskeleton-intermediate filament, snail, slug, E-adherin, ZO-1, beta-catenin, desmoplakin, claudin, and collagen, which is caused by TM4SF5 expression, by comparing the expression to a control group not treated with the candidate material of step 1).

4. The method for screening a material for treating hepatic fibrosis according to claim 3, wherein the TM4SF5 protein is the polypeptide of SEQ. ID. NO: 2.

* * * * *